US012796912B2

(12) United States Patent
Bex et al.

(10) Patent No.: US 12,796,912 B2
(45) Date of Patent: Nov. 17, 2026

(54) METHOD FOR VISUAL FUNCTION ASSESSMENT

(71) Applicant: Northeastern University, Boston, MA (US)

(72) Inventors: Peter Bex, Conford, MA (US); Jan Skerswetat, Boston, MA (US)

(73) Assignee: Northeastern University, Boston, MA (US)

( * ) Notice: Subject to any disclaimer, the term of this patent is extended or adjusted under 35 U.S.C. 154(b) by 614 days.

(21) Appl. No.: 18/022,816

(22) PCT Filed: Sep. 7, 2021

(86) PCT No.: PCT/US2021/049250
§ 371 (c)(1),
(2) Date: Feb. 23, 2023

(87) PCT Pub. No.: WO2022/051710
PCT Pub. Date: Mar. 10, 2022

(65) Prior Publication Data

US 2023/0309818 A1 Oct. 5, 2023

Related U.S. Application Data

(60) Provisional application No. 63/075,084, filed on Sep. 4, 2020.

(51) Int. Cl.
*A61B 3/032* (2006.01)
*A61B 3/00* (2006.01)

(52) U.S. Cl.
CPC ............ *A61B 3/032* (2013.01); *A61B 3/0033* (2013.01); *A61B 3/0041* (2013.01)

(58) Field of Classification Search
CPC ..... A61B 3/032; A61B 3/0033; A61B 3/0041; A61B 5/168; A61B 3/028; A61B 3/036;
(Continued)

(56) References Cited

U.S. PATENT DOCUMENTS 5,589,897 A * 12/1996 Sinclair .................. A61B 3/024 351/239
6,527,391 B1 * 3/2003 Heijl ...................... A61B 3/024 351/243
(Continued)

FOREIGN PATENT DOCUMENTS

WO 2003017256 A1 2/2003
WO 2013046064 A1 4/2013
(Continued)

OTHER PUBLICATIONS

Spiegel et al., "First- and second-order contrast sensitivity functions reveal disrupted visual processing following mild traumatic brain injury", Vision Research 122 (2016) pp. 43-50.

*Primary Examiner* — Jeffrey G. Hoekstra
(74) *Attorney, Agent, or Firm* — Adams & Reese LLP

(57) ABSTRACT

Methods and devices for rapid, self-administered, and adaptive testing of a wide variety of visual and neurological impairments are based on graphical presentation to a subject of visual stimuli of varying intensity. Psychometric functions are used to determine the subjects sensitivity to selected stimuli. Diagnosis of ophthalmic, optometric, and/or neurologic conditions is achieved from the subjects stimulus sensitivity pattern.

32 Claims, 14 Drawing Sheets

(58) Field of Classification Search
CPC ....... A61B 3/066; A61B 5/165; A61B 5/4082; A61B 5/4088
See application file for complete search history.

(56) References Cited

U.S. PATENT DOCUMENTS

| | | | | |
|---|---|---|---|---|
| 8,702,238 | B2 * | 4/2014 | Berry | G16H 40/63 351/246 |
| 2002/0024634 | A1 * | 2/2002 | Fink | A61B 3/024 351/237 |
| 2007/0134636 | A1 | 6/2007 | Chan et al. | |
| 2009/0271740 | A1 | 10/2009 | Ryan-Hutton et al. | |
| 2011/0187994 | A1 | 8/2011 | Erickson et al. | |
| 2012/0050685 | A1 | 3/2012 | Bartlett et al. | |
| 2012/0236262 | A1 | 9/2012 | Johansson | |
| 2015/0150444 | A1 | 6/2015 | Bex et al. | |
| 2018/0263487 | A1 | 9/2018 | Robson | |
| 2019/0008381 | A1 | 1/2019 | Rotenstreich et al. | |
| 2020/0121179 | A1 | 4/2020 | Prusky et al. | |
| 2020/0329961 | A1 * | 10/2020 | Oz | A61B 3/08 |

FOREIGN PATENT DOCUMENTS

| | | | | |
|---|---|---|---|---|
| WO | 2013170091 | A1 | 11/2013 | |
| WO | 2015027218 | A1 | 2/2015 | |
| WO | 2015027225 | A1 | 2/2015 | |
| WO | 2015179539 | A1 | 11/2015 | |
| WO | WO-2016084086 | A1 * | 6/2016 | A61B 3/036 |
| WO | WO-2017070704 | A2 * | 4/2017 | A61B 3/032 |

* cited by examiner

METHOD FOR VISUAL FUNCTION ASSESSMENT

STATEMENT REGARDING FEDERALLY SPONSORED RESEARCH OR DEVELOPMENT

This invention was made with government support under EY032162, and EY029713 awarded by the National Institutes of Health. The government has certain rights in the invention.

BACKGROUND

Vision screening in both clinical and basic science is a critical step that quantifies functional deficits in the visual system. In clinical practice, vision screening is essential for disease diagnosis and monitoring. In basic science, it can quantify sensory or perceptual performance or ensure that research participants meet specific study inclusion or exclusion criteria.

Recent social distancing measures and developments in communication, display and sensor technologies mean that remote vision screening may play a significant role in teleophthalmology. Clinical guidelines recommend vision screening at multiple year intervals. However, significant vision changes could go undetected in these long intervals, especially for gradual loss. Self-administered vision screening can serve an important home monitoring role between clinic visits, particularly in remote and medically underserved locations.

The human visual system includes multiple interdependent pathways that are structurally and functionally specialized and may be selectively affected across the lifespan. Comprehensive vision screening therefore ideally requires the administration of multiple tests that assess the integrity of different visual pathways. However, practical limitations limit the number of tests that can be administered. Furthermore, in many cases, vision tests require the subject to learn a new task or a new set of stimuli for each test and to complete many trials where they are forced to guess because the paradigm requires the presentation of sub-threshold stimuli. These factors can be frustrating for subjects and may confound attention, learning and memory effects with visual function deficits. Existing technology requires compromises in the number and duration of tests administered, with the risk that the vision screening is inaccurate due to noisy or under-constrained data, or incomplete because only a subset of tests is administered.

SUMMARY

The present technology provides methods and devices for rapid, self-administered, and adaptive testing of a wide variety of visual and neurological impairments. The methods are based on graphical presentation to a subject of visual stimuli of graded intensity and the use of psychometric functions to determine the subject's sensitivity to selected stimuli. Diagnosis of ophthalmic, optometric, and/or neurologic conditions is achieved from the subject's stimulus sensitivity pattern.

The technology can be further summarized by the following list of features.

1. A method for testing a visual or neurological function of a human subject, the method comprising:
   (a) providing a device having a graphical display and a user input;
   (b) displaying sequentially a set of grids on the display, each grid comprising a plurality of cells; wherein each grid comprises a visual stimulus displayed in two or more of the cells of the grid; wherein the visual stimulus displayed within a grid varies in intensity from cell to cell; and wherein the stimulus displayed for each grid differs from the stimulus displayed for at least one other grid of the set;
   (c) receiving subject responses through the user input, the responses indicating a perceived characteristic of the stimulus for each cell of each displayed grid; and
   (d) analyzing the subject responses from each grid using a sensitivity function to obtain the subject's responsiveness to each of the stimuli in the set of grids, said responsiveness characterized as a probability of reporting the stimulus as a function of stimulus intensity.
2. The method of feature 1, further comprising:
   (e) analyzing the subject's responsiveness to two or more of the stimuli of the set of grids to obtain a pattern of responsiveness of the subject.
3. The method of feature 2, further comprising:
   (f) comparing the subject's pattern of responsiveness to one or more known patterns of responsiveness; and
   (g) identifying a presence or absence in the subject, or a likelihood thereof, of one or more visual or neurological conditions.
4. The method of any of the preceding features, wherein the perceived characteristic of the stimulus comprises one or more stimulus characteristics selected from the group consisting of absence, presence, luminance, contrast, color, depth, motion, flicker, spatial form, object recognition, object shape, object form, object size, facial recognition, facial feature recognition, feature position, feature angle, spatial resolution, noise-defined depth, and sparse-pattern depth.
5. The method of any of the preceding features, wherein the stimulus intensity within a grid spans a range from difficult-to-detect to easy-to-detect for the subject.
6. The method of any of the preceding features, wherein the position of stimulus-containing within the grid is random or non-random.
7. The method of any of the preceding features, wherein the stimuli in the cells of each grid are displayed only one at a time, with all other cells of the grid remaining blank until the subject's response is obtained for the displayed cell.
8. The method of any of the preceding features, wherein format of one or more grids comprises a variable number of rows and columns.
9. The method of any of the preceding features, wherein one or more grids are displayed for each stimulus.
10. The method of any of the preceding features, wherein stimulus type or stimulus intensity within a grid are varied from an earlier presented grid based upon subject responses.
11. The method of any of the preceding features, wherein the subject responds for each cell of a grid whether the stimulus is present or not present in the cell, and wherein the subject's sensitivity to the stimulus displayed in each grid is calculated.
12. The method of any of the preceding features, wherein the subject indicates a degree of confidence in their response for each cell based on a position of their response or a secondary response.

13. The method of any of the preceding features, wherein the sensitivity function is a d-prime function, defined as:

$$d'(s) = \frac{\beta(s/\tau)^{\gamma}}{\sqrt{(\beta^2 - 1) + (s/\tau)^{2\gamma}}}$$

where $\tau$ is the sensitivity threshold (stimulus intensity where d'=1), $\beta$ is an upper asymptote of the saturating function (stimulus intensity where d'=5), s is signal intensity, and $\gamma$ is slope of the function; and wherein d'(s) is related to the probability of the subject reporting the presence of the stimulus as a function of stimulus intensity by the following psychometric function:

$$\Psi_{yes}(s) = 1 - G(z(i - \Psi_{yes}(0) - d'(s))$$

where G(s) is a cumulative Gaussian function, z is a z-score, and $\Psi_{yes}(0)$ is false alarm rate.

14. The method of feature 13, wherein the psychometric function is computed on-the-fly for each grid and is used to estimate a stimulus for which d'=0.1, which is very difficult for the subject to detect, and a stimulus intensity for which d'=4.5, which is very easy for the subject to detect.

15. The method of any of feature 13 or 14, wherein the test is optimized for the subject by performing two or more trials of the set of grids, wherein the stimulus intensities on the first trial are based on data from previous observers or on physical stimulus limits of the display, and wherein the stimulus intensities on subsequent trials are based on the estimate of sensitivity computed for all previous grids for the current observer.

16. The method of any of the preceding features, wherein both threshold stimulus intensity and suprathreshold performance of the subject are determined.

17. The method of feature 16, wherein individual cells comprise two or more stimuli, and the subject's response comprises discrimination between the two or more stimuli.

18. The method of any of features 1-12, wherein the sensitivity function is an orientation error function, defined as:

$$\tau_{\theta}(s) = \left(\theta_i + \left(\frac{\pi}{2} - \theta_i\right)\right)\left(0.5 + 0.5 * \mathrm{erf}\left(\frac{s - \tau}{\sqrt{2}\gamma}\right)\right)$$

where $\tau$ is a sensitivity threshold, $\theta_i$ is intrinsic orientation uncertainty within the subject's visual system, s is signal intensity and $\gamma$ is the slope of the function.

19. The method of any of features 1-12, wherein the sensitivity function is a cumulative Gaussian function, defined as:

$$\tau(s) = (p_{guess} + (1 - p_{guess}))\left(0.5 + 0.5 * \mathrm{erf}\left(\frac{s - \tau}{\sqrt{2}\gamma}\right)\right)$$

where $\tau$ is a sensitivity threshold, $p_{guess}$ is the probability of a correct response for a guess (equal to the reciprocal of the number of alternative response choices), s is signal intensity and $\gamma$ is the slope of the function.

20. The method of any of features 1-12, wherein sensitivity to one or more of the stimuli can vary in two or more dimensions, and wherein a known relationship exists between said one or more stimuli and two or more types of subject sensitivity thereto.

21. The method of feature 20, wherein the two or more types of subject sensitivity comprise spatial frequency and contrast, and wherein the known relationship is defined by:

$$S_{LP}(f : f_0, b, a) = 10^{-\left(\frac{\log_{10}(f/f_0)}{b}\right)^2}$$
$$= 1 - a \quad f < f_0 \text{ and } s_{LP} < 1 - a.$$

22. The method of feature 20, wherein the two or more types of subject sensitivity comprise spatial frequency, temporal frequency, and contrast, and wherein the known relationship is defined by:

$$CSF(\rho, v_k) = k \cdot c_0 \cdot c_1 \cdot c_2 \cdot v_k \cdot (c_1 2\pi\rho)^2 \exp\left(-\frac{c_1 4\pi\rho}{\rho_{max}}\right)$$
$$\text{where } k = s_1 + s_2 \cdot |\log(c_2 v_R / 3)|^3$$
$$\text{and } \rho_{max} = \frac{p_1}{(c_2 v_R + 2)}.$$

23. The method of feature 20, wherein the two or more types of subject sensitivity comprise color saturation and hue angle, and wherein the known relationship is defined by:

$$\tau(s) = \frac{(x - h)^2}{a^2} + \frac{(y - k)^2}{b^2}$$

wherein $\tau$ is visual color sensitivity for stimulus sensitivity s, h is hue angle, and k is color saturation.

24. The method of feature 20, wherein the two or more types of subject sensitivity comprise stimulus variance and response variance, and wherein the known relationship is defined by an equivalent noise function defined as:

$$\tau(s) = \sqrt{\frac{\sigma_{int}^2 + \sigma_{ext}^2}{N_{samp}}}$$

wherein $\tau$ is visual detection threshold for stimulus intensity s, $\sigma_{int}$ is intrinsic noise in the observer's visual system, $\sigma_{iex}$ is external noise in the stimulus, and $N_{samp}$ is sampling efficiency, corresponding to the number of stimulus samples employed by the observer.

25. The method of feature 20, wherein the two or more types of subject sensitivity comprise stimulus pedestal intensity and sensitivity, and wherein the known relationship is defined by a dipper or threshold versus intensity function defined as:

$$\tau(s) = \sqrt{\left(1 + \frac{1}{S}\right)(\sigma_{int}^2 + \sigma_{ext}^2)} - \sigma_{ext}$$

wherein $\tau$ is visual detection threshold for stimulus intensity s, $\sigma_{int}$ is intrinsic noise in the observer's visual system, $\sigma_{iex}$ is the intensity of the stimulus pedestal, and S is the discrimination criterion employed by the observer.

26. The method of any of the preceding features, wherein the subject provides responses using a touch-sensitive display screen, computer pointing device, or speech recognition software.
27. The method of any of the preceding features, wherein the method is supervised or self-administered by the subject outside of a medical facility, vision testing facility, or doctor's office.
28. The method of any of the preceding features, wherein the method is repeated after one or more time intervals.
29. The method of any of the preceding features, wherein the method is used to detect and/or monitor the progression of an ophthalmic condition, an optometric condition, or a neurologic disease or condition.
30. The method of feature 29, wherein the ophthalmic disease or condition is selected from the group consisting of age-related macular degeneration and other disorders of early visual neural pathways; diabetic retinopathy; color vision deficit; glaucoma; and amblyopia.
31. The method of feature 29, wherein the optometric condition is selected from the group consisting of myopia, hyperopia, and other optical aberrations of lower and higher order; presbyopia; astigmatism; and cataract, corneal edema, and other changes in optical opacity.
32. The method of feature 29, wherein an optometric or ophthalmic condition is detected or monitored, and wherein visual acuity is determined using as stimulus an oriented arc in each cell, wherein the arc comprises a gap whose angular position is registered by the subject as a measure of arc orientation.
33. The method of feature 32, wherein the arc comprises a line width that is ⅕ of the arc diameter and the gap angle is equal to the line width.
34. The method of feature 32, wherein the angular position of the gap is registered by the subject at a cell boundary as a measure of arc orientation.
35. The method of feature 32, wherein a series of cells are provided to the subject in which stimulus detection spans a range personalized for the subject from easily visible to subthreshold visible.
36. The method of feature 32, wherein a series of cells are provided to the subject in which stimulus detection spans a range from easily visible for a person with 20/200 vision to subthreshold for a person with 20/10 vision.
37. The method of feature 32, wherein the subject's visual function based on performance on previous grids is atypical and stimulus dimensions are extended.
38. The method of feature 32, wherein the stimulus luminance and background luminance are adjusted to measure the subject's performance across a range of luminance and contrast conditions.
39. The method of feature 32, wherein luminance intensity and size of a cell boundary are adjusted to generate a glare source.
40. The method of any of features 32-39, wherein the method is used to determine and/or monitor a visual correction of the subject.
41. The method of feature 29, wherein the neurologic disease or condition is selected from the group consisting of concussion, traumatic brain injury, traumatic eye injury, and other types of neurological trauma; cognitive impairment, Autism Spectrum Condition (ASC), Attention Deficit Disorder (ADD), and other high level neurological disorders; and schizophrenia, depression, bipolar disorder, and other psychotic disorders.
42. The method of feature 41, wherein the neurologic disease or condition detected or monitored is selected from the group consisting of prosopagnosia, object agnosia, and affective disorders, and wherein a series of cells comprising face or object images are presented to the subject in which stimulus pairs comprising a first stimulus category and a second stimulus category are progressively blended, and wherein the subject's response comprises identifying for each cell whether the first stimulus category or the second stimulus category is displayed.
43. The method of feature 42, wherein the stimulus pairs comprise objects, animals, faces of different identity, faces displaying different emotion, and faces of different gender.
44. The method of any of features 29-43, wherein said detection and/or monitoring of the progression of an ophthalmic condition, an optometric condition, or a neurologic disease or condition comprises analysis of a pattern of sensitivities as shown in Table 1.
45. A device for performing the method of any of the preceding features, the device comprising a graphic display, a user input, a processor, a memory, optionally wherein the processor and/or memory comprise instructions for performing said method.

BRIEF DESCRIPTION OF THE DRAWINGS

FIG. 1A shows a grid containing in certain cells visual objects having differing degrees of contrast. FIG. 1B shows a grid containing in certain cells a specified spatial form (circular pattern with different degrees of organization), while other cells have a more random pattern. FIG. 1C shows a grid containing in certain cells a noise-defined depth pattern of varying intensity. FIG. 1D shows a grid containing cells having a sparse-pattern with varying depth. FIG. 1E shows a grid having in certain cells colored objects of varying color saturation.

DETAILED DESCRIPTION

Figure 1A:
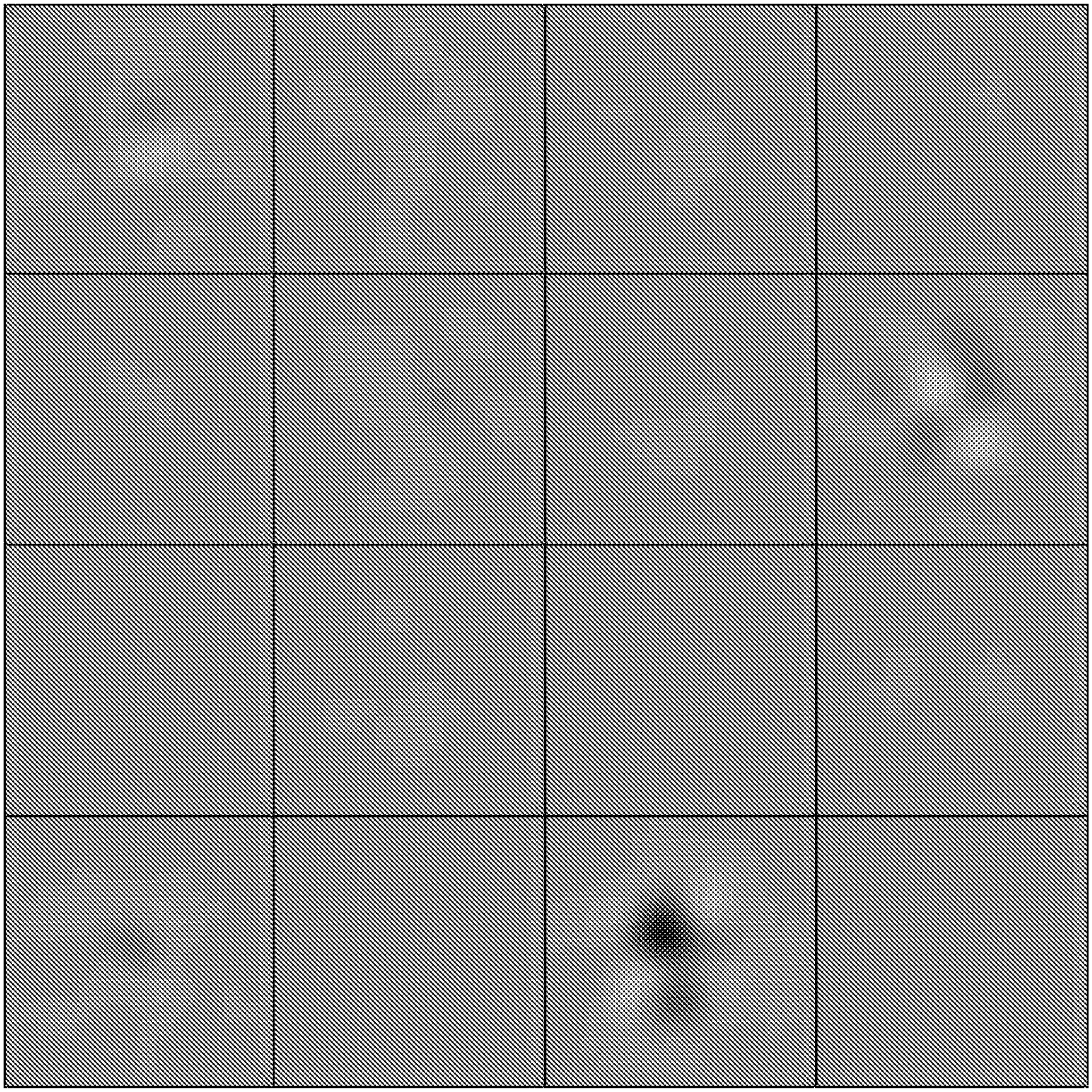
FIGS. 1A-1E show examples of grids used in methods of visual function assessment according to the present technology. A grid or matrix of cells, such as those shown in each of FIGS. 1A-1E, is presented to a human subject. In each matrix, some cells contain a stimulus, but some are empty. The signal intensity of the stimulus in each call spans a range from extremely difficult to very easy. The observer selects cells containing a stimulus, such as by using a computer mouse or a touch screen. Cells selected by the subject as having the stimulus are marked with a ring.
Figure 1B:
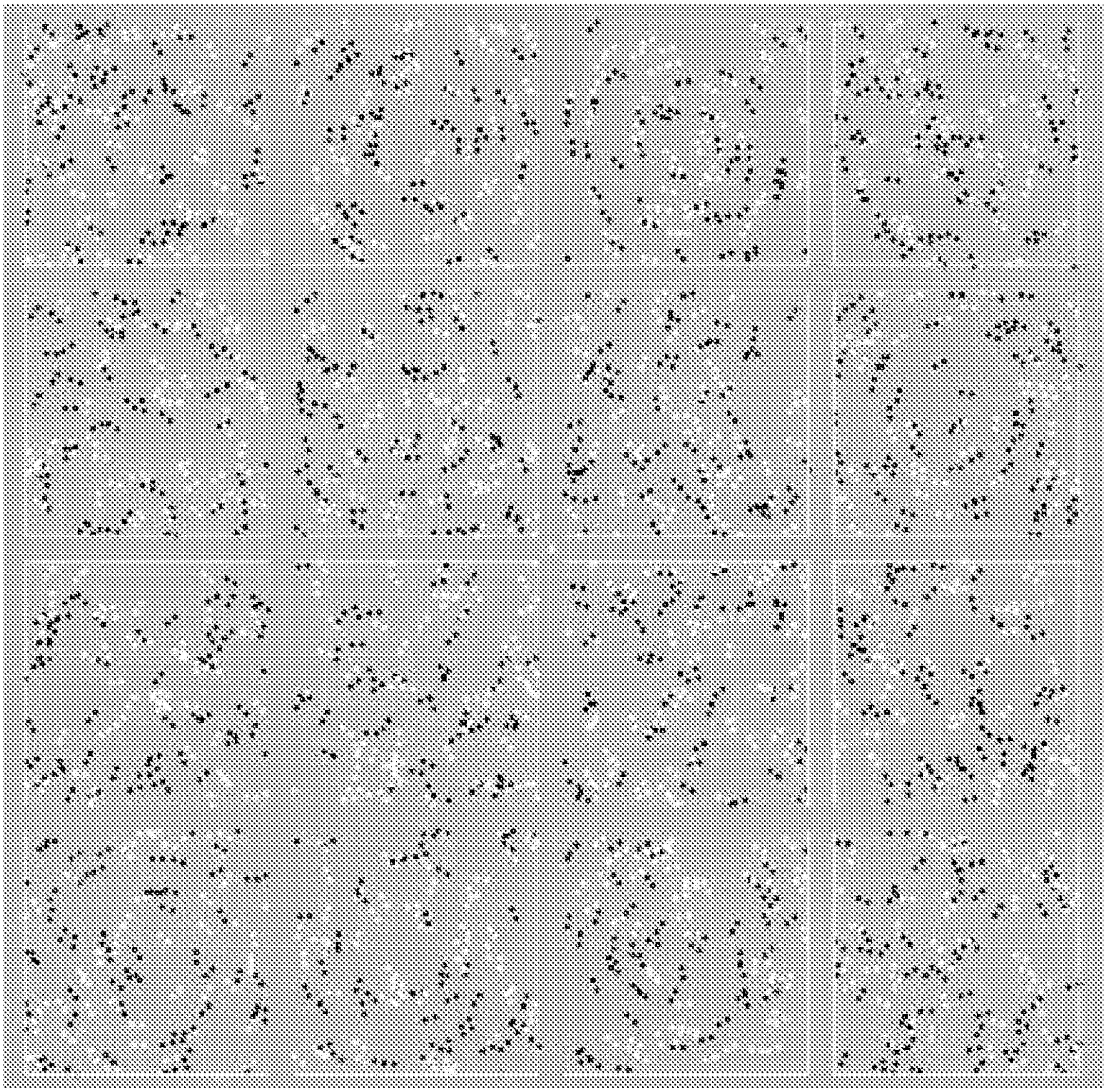
Figure 1C:
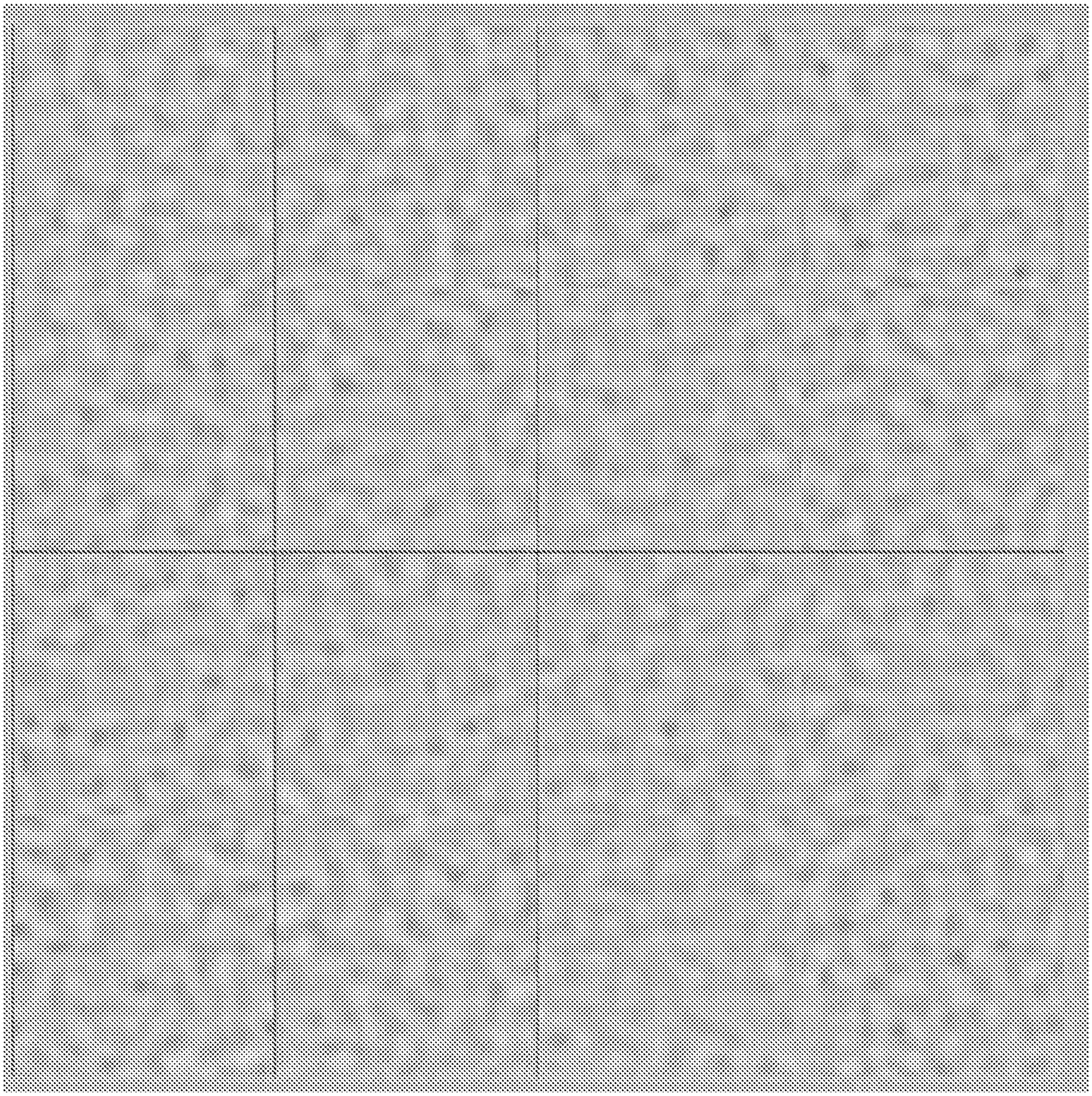
Figure 1D:
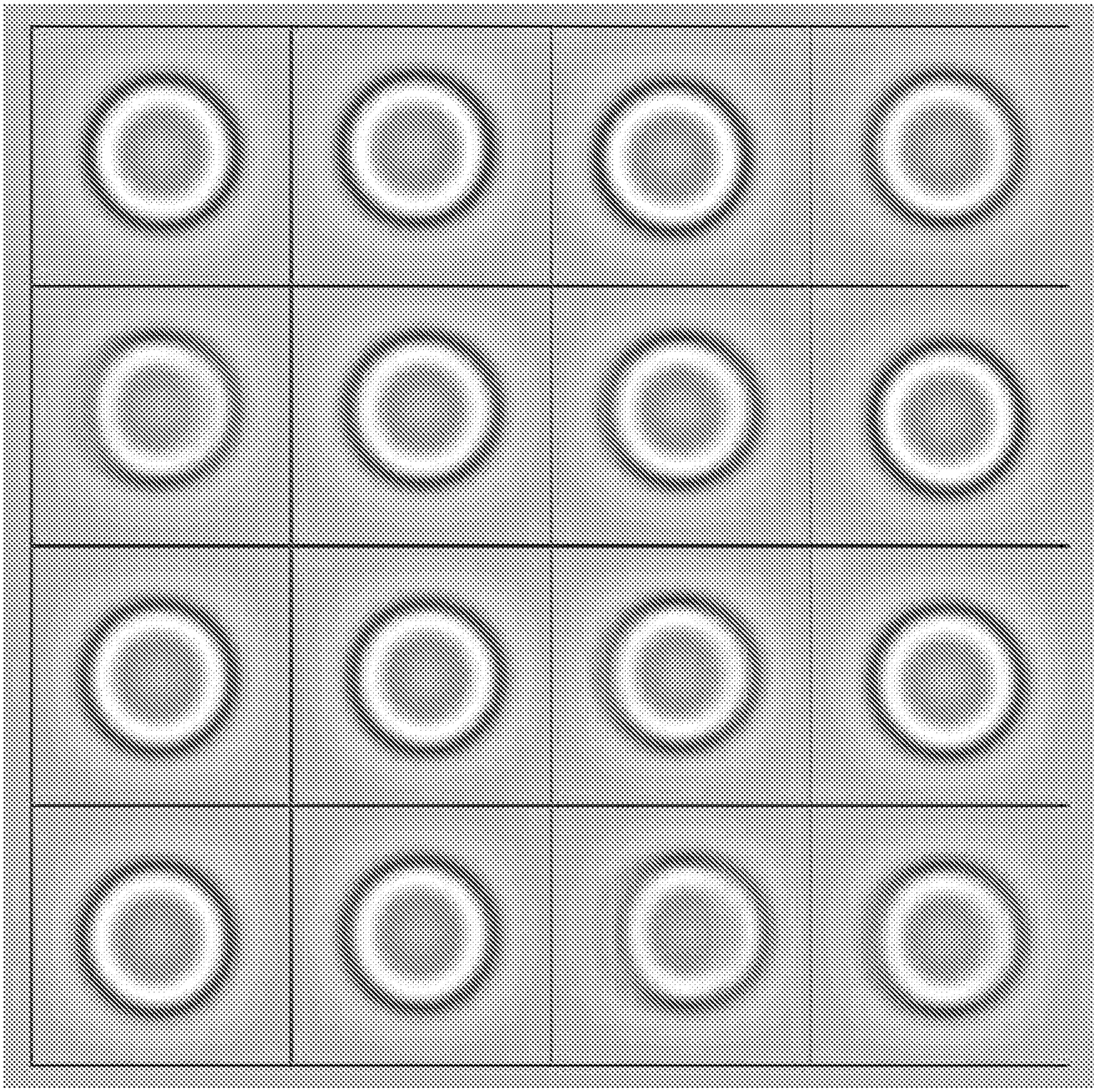
Figure 1E:
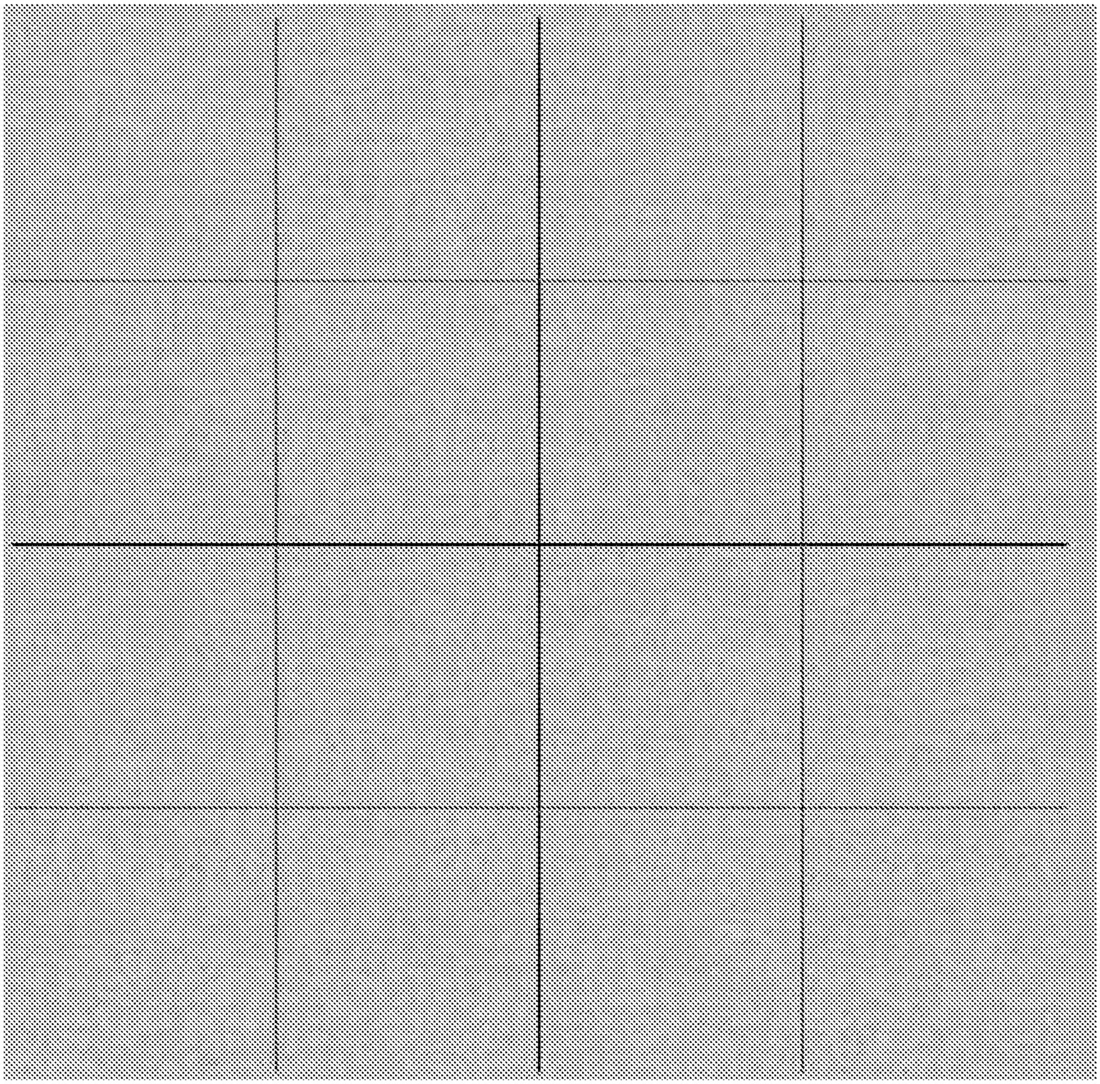

The present technology provides rapid and easy-to-administer methods for comprehensively assessing visual function as well as neurological function in humans.

One aspect of the technology is a method for testing a visual or neurological function of a human subject. The method includes the steps of: (a) providing a device having a graphical display and a user input device or function; (b) displaying sequentially a set of grids on the display, each grid comprising a plurality of cells in which a visual stimulus can be displayed; (c) receiving subject responses through the user input, wherein the subject identifies at least which cells contain the stimulus; and (d) analyzing the subject responses from each grid using a sensitivity function to obtain the subject's responsiveness to each of the stimuli in the set of grids. The sensitivity function describes the probability of the subject reporting the stimulus as a function of stimulus intensity. Optionally, the method also can include the further step of: (e) analyzing the subject's responsiveness to two or more different stimuli of the set of grids to obtain a pattern of responsiveness of the subject. As a further option, the method can still further include the steps of: (f) comparing the subject's pattern of responsiveness to one or more known patterns of responsiveness; and (g) identifying a presence or absence in the subject, or a likelihood thereof, of one or more visual or neurological conditions.

The method can be carried out on any general purpose computational device, such as a personal computer, laptop, tablet, or mobile phone, or on a special purpose device that has a graphical display and a user input function, such as a touch screen, pointing device such as a mouse or trackball, keyboard, buttons, or a microphone or headset together with speech recognition software. The device can further include one or more speakers for presenting instructions, commands, or auditory stimuli. The method is well suited for self-administration by the subject in any environment, such as home or office, without or with assistance by a trained person. The computer or other device can optionally transmit results of the subject's test to a remote facility for further analysis or for attention by a medical or optometric professional. The computer or special purpose device can be portable and battery operated for use in the field, such as at a sports event or on a battlefield. A computer or other device used for conducting the tests will include a display, input device, processor, memory, and preferably a radio transceiver for wireless communication. The processor and/or memory can be pre-loaded with software for implementing the test, calculating results, storing results, and transmitting results to another computer or other device.

The display is preferably a color display capable of high resolution graphical representation of images with or without animation (changes in the image over time). A preferred presentation of the test images is in the form of a grid or matrix composed of a number of cells that are similar or identical in size and shape, although images also can be presented single on the display or in other arrangements, including random or patterned arrangements. A grid typically presents a rectangular ordering of cells, and the cells can themselves be rectangular, square, round, elliptical, or have another shape. Such a rectangular array can have any desired number of cells arranged in rows and columns. For example, a grid can have cells arranged in a 2×2, 2×3, 2×4, 2×5, 2×6, 3×2, 3×3, 3×4, 3×5, 3×6, 4×2, 4×3, 4×4, 4×5, 4×6, 5×2, 5×3, 5×4, 5×5, 5×6, 6×2, 6×3, 6×4, 6×5, or 6×6 grid (rows×columns), or another arrangement. The format of grids within a set can be the same or different. The cells of a grid can be arranged in any desired two-dimensional arrangement, such as a square or rectangular grid containing 3, 4, 6, 8, 9, 10, 12, 15, 16, 20, 24, 25, 27, 30 or more cells, or a different arrangement. A set can include any number of grids, such as 2, 3, 4, 5, 6, 7, 8, 9, 10, 12, 15, 20, 30, 40, 50, or more grids.

The cells of a grid preferably will display either no stimulus or a single type of stimulus, wherein the intensity of the stimulus varies from cell-to-cell containing the stimulus. The set of grids can contain a different stimulus in each grid, or two or more grids of the set can contain the same stimulus presented identically or differently in cell arrangement or intensity range. A set of grids can contain any number of different stimuli, such as 1, 2, 3, 4, 5, 6, 7, 8, 9, or 10 or more different stimuli. A set of grids can also present one or more types of different stimuli over different ranges of intensity, the range presented in a single grid or spread out over two or more grids.

A stimulus can be a characteristic of a visual object that is perceived by the subject. For example, the perceived characteristic of a stimulus can be absence, presence, luminance, contrast, color, depth, motion, flicker, spatial form, object recognition, object shape, object form, object size, facial recognition, facial feature recognition, feature position, feature angle, spatial resolution, noise-defined depth, and sparse-pattern depth of a visual object or pattern, and can be optionally supplemented by change over time or space or the addition of an auditory stimulus. Preferably the perceived characteristic is the same for all cells of a grid in which it appears, and the strength, intensity, or detectability by the subject varies within the grid. Preferably the range of stimulus strength, intensity, or detectability encompasses barely detectable characteristics as well as easily detectable characteristics. The position in a grid of cells containing or not containing a stimulus, or containing varying intensities of the stimulus, can be random, or can be selected according to a desired pattern. Stimuli or the range of their intensity also can be displayed adaptively, such that the subject's sensitivity is calculated on the fly and used to alter the stimulus or range of intensity in subsequent cells, grids, or sets of grids. Examples of grids with visual stimuli are shown in FIGS. 1A-1E.

Figure 6:
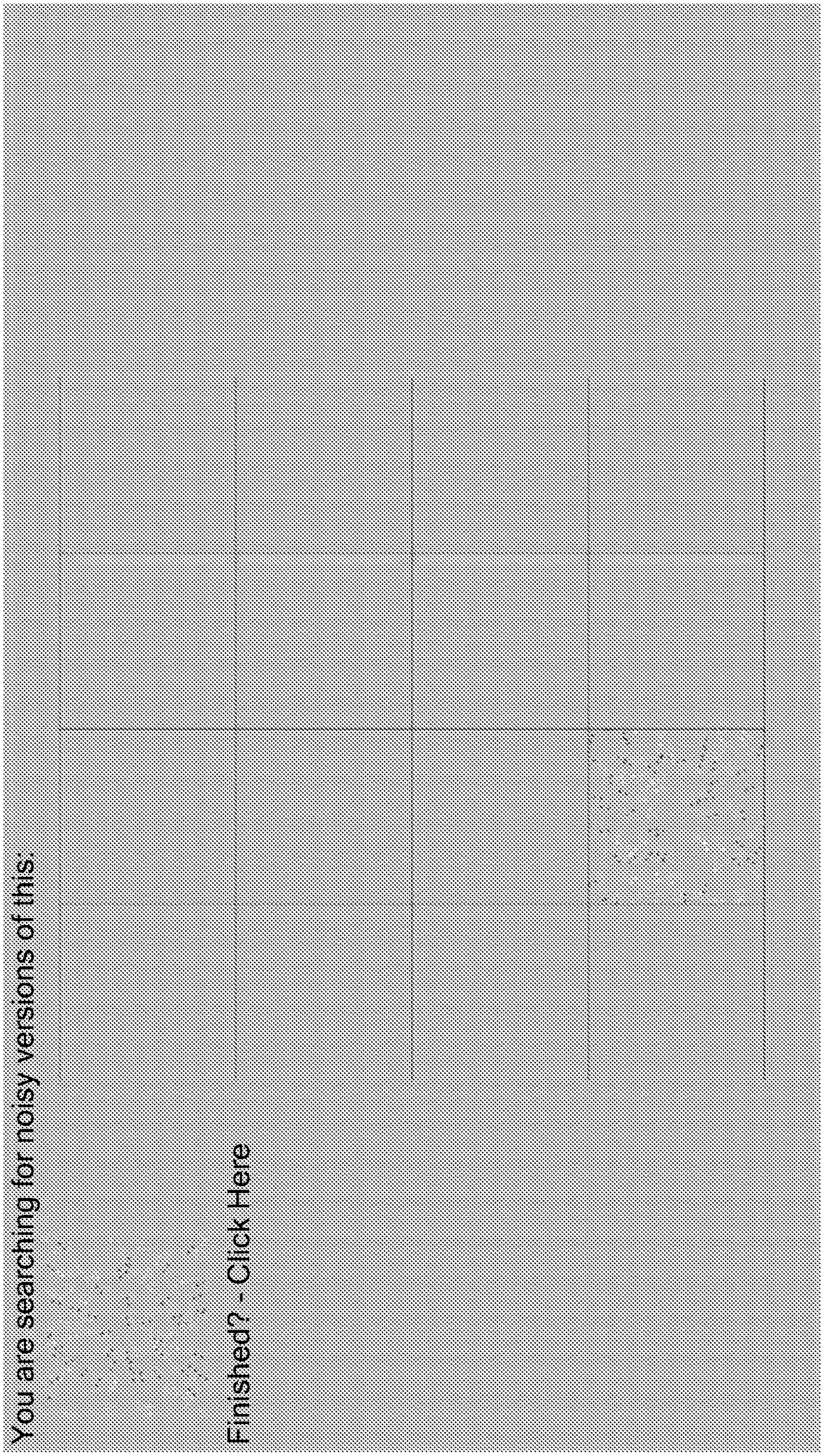
FIG. 6 Illustrates a grid presented with a hidden cell paradigm. To avoid interference from adjacent cells, only the stimulus in the cell at the location of gaze or the cursor is presented at a given time. Subjects explore the grid by looking around or moving the cursor around and respond one cell at a time, without other cells visible.

Optionally, cells can be displayed individually, with other cells of the grid not displayed, so as to avoid distracting the subject or interactions between cells in the eyes or mind of the subject. Pattern perception and motion perception stimuli can be affected by the presence of multiple stimuli. Sensitivity to motion and pattern stimuli can be superior in the peripheral visual field than in central vision. This means that a target may be visible in a cell away from the current gaze direction and no longer be visible when the subject directly views the cell, which can be confusing. Additionally, sensitivity to the stimulus in a given cell may be affected by stimuli in adjacent cells for certain tasks. To avoid such effects, a hidden cell paradigm can be implemented in which only the cell beneath the mouse is presented at any time (see FIG. 6).

In addition to selecting any cells where the subject detects a target stimulus, additional response parameters can be recorded and scored. For example, the subject's confidence in their response can be indicated by clicking in a different location in the cell. For example, an observer can indicate low confidence of their response by clicking to the left side of the cell, or high confidence in their response by clicking on the right side of the cell. The two dimensions of the cell (vertical and horizontal, or radial and rotational) can be used to score separate parameters (e.g., apparent age of a face on the horizontal axis and apparent gender on the vertical axis).

After the subject has selected all cells that they think contain a stimulus, a computer algorithm can classify the response in each cell as follows:

Hit (Correct: target present and selected by the subject)

Miss (Incorrect: target present but not selected by the subject),

False Alarm (Incorrect: target absent but selected by the subject) or

Correct Rejection (Correct: target absent and not selected by the subject)

Signal detection theory can be used to estimate sensitivity for each stimulus intensity. For example the function called d-prime (d'), shown below, can be used. The data are fit with a psychometric function to generate an updated estimate of d-prime (d') for this observer for this task:

$$d'(s) = \frac{\beta(s/\tau)^{\gamma}}{\sqrt{(\beta^2 - 1) + (s/\tau)^{2\gamma}}}$$

where τ is the sensitivity threshold (i.e., the stimulus intensity where d'=1), β is the upper asymptote of the saturating function (i.e., the stimulus intensity where d'=5), s is signal intensity, and γ is the slope of the function.

Figure 1F:
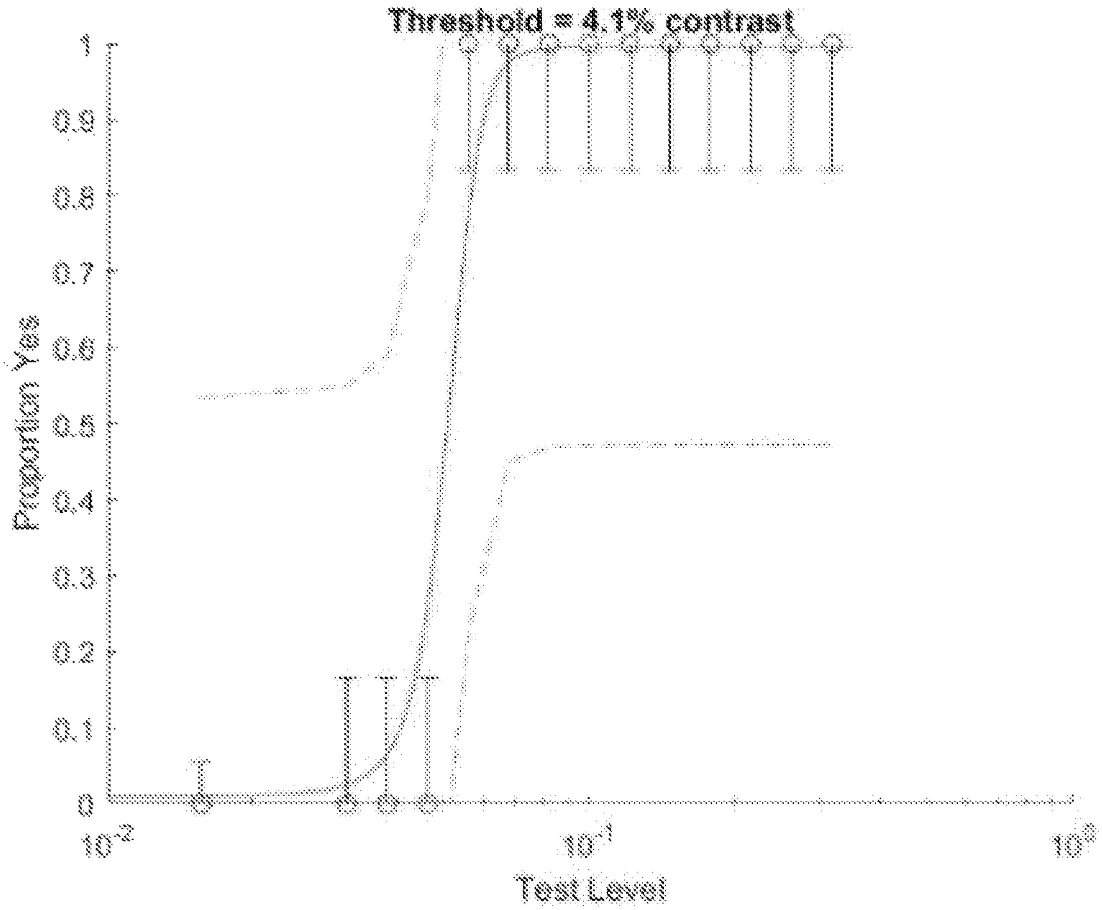
FIG. 1F shows a plot of a d' psychometric function of the probability of reporting the stimulus as a function of stimulus intensity.

The d-prime function can be related to the psychometric function of the probability of reporting the presence of a stimulus as a function of its intensity (illustrated in FIG. 1F):

$$\Phi_{yes}(s) = 1 - G(z(1 - \Psi_{yes}(0) - d'(s))$$

where G(s) is a cumulative Gaussian function, and $\Psi_{yes}(0)$ is the false alarm rate.

The psychometric function can be computed on-the-fly for each matrix, and can be used to estimate a stimulus for which d-prime=0.1, which is extremely difficult to detect, and a stimulus intensity for which d-prime=4.5, which is very easy to detect.

An alternative sensitivity function is an Orientation Error function, defined as:

$$\tau_{\theta}(s) = \left(\theta_i + \left(\frac{\pi}{2} - \theta_i\right)\right)\left(0.5 + 0.5 * \text{erf}\left(\frac{s-\tau}{\sqrt{2}\gamma}\right)\right)$$

where τ is a sensitivity threshold, $\theta_i$ is internal orientation uncertainty, s is signal intensity and γ is the slope of the function.

Other functions include a cumulative Gaussian function, defined as:

$$\tau(s) = (p_{guess} + (1 - p_{guess}))\left(0.5 + 0.5 * \text{erf}\left(\frac{s-\tau}{\sqrt{2}\gamma}\right)\right)$$

where τ is a sensitivity threshold, $p_{guess}$ is the probability of a correct response for a guess (equal to the reciprocal of the number of alternative response choices), s is signal intensity and γ is the slope of the function.

The stimuli in each matrix can be chosen to span the range from difficult to easy. The number of signal stimuli preferably is random on each trial, and their position in the matrix preferably is random on each trial. The stimulus intensities on the first trial can be based on data from previous observers (e.g., typical sensitivity for comparable subjects) or can be based on physical stimulus limits (e.g. color gamut of a display). The stimulus intensities on subsequent stimuli can be based on the estimate of d-prime or another psychometric function computed for all previous grids for the current subject, which optimizes the test for each subject. At the end of the test, visual sensitivity can be computed from all responses to all cells.

An implementation of the present technology can utilize the Psychtoolbox open source software (see psychtoolbox-.org/credits). Other software also can be used.

Any of the tests, algorithms, systems, or devices described in WO2013170091 A1, which is hereby incorporated by reference in its entirety, can be used in the present technology.

Figure 2A:
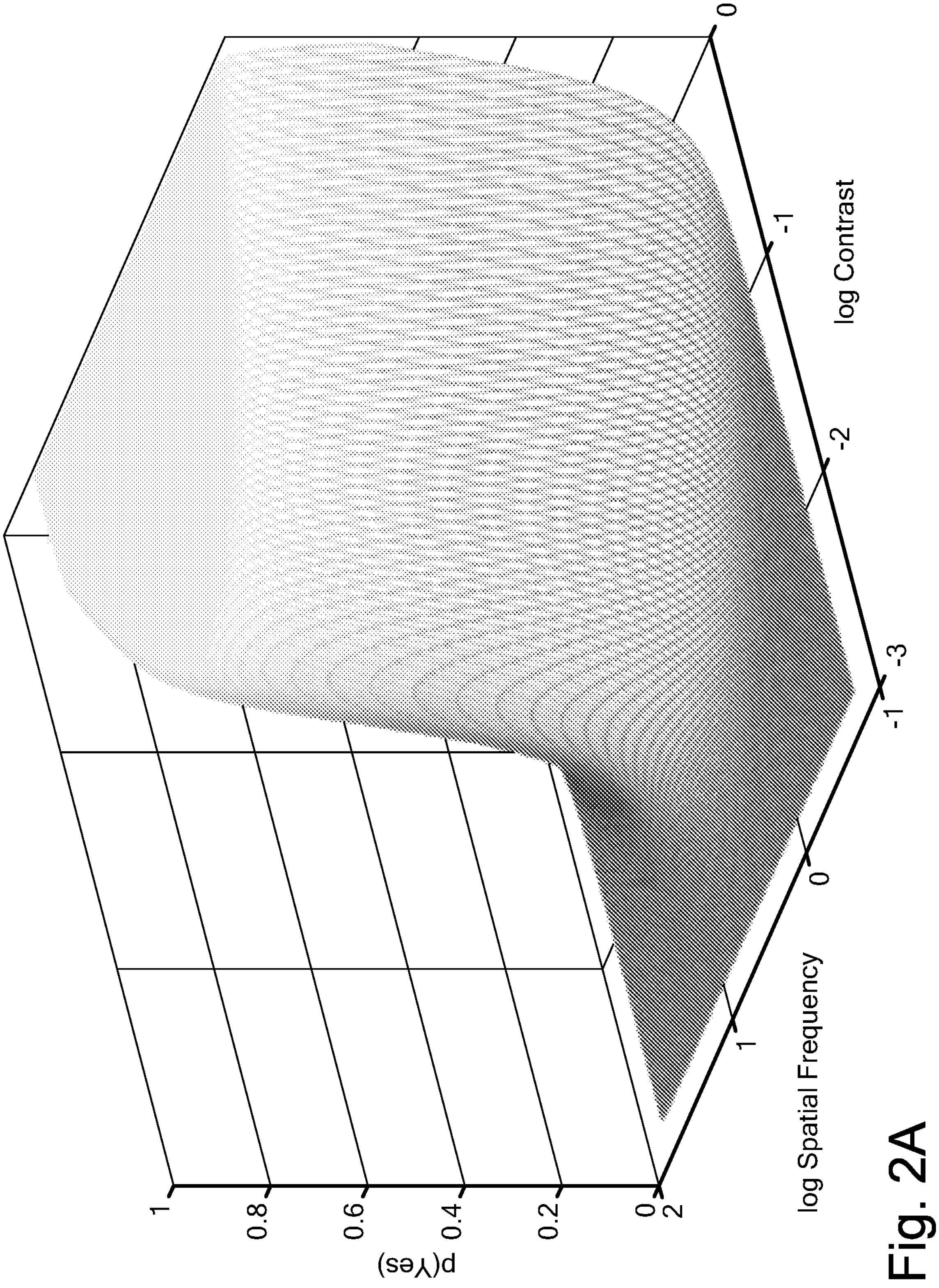
FIG. 2A illustrates a psychometric function showing the probability of reporting a stimulus as a function of two variables, contrast and spatial frequency.
Figure 2B:
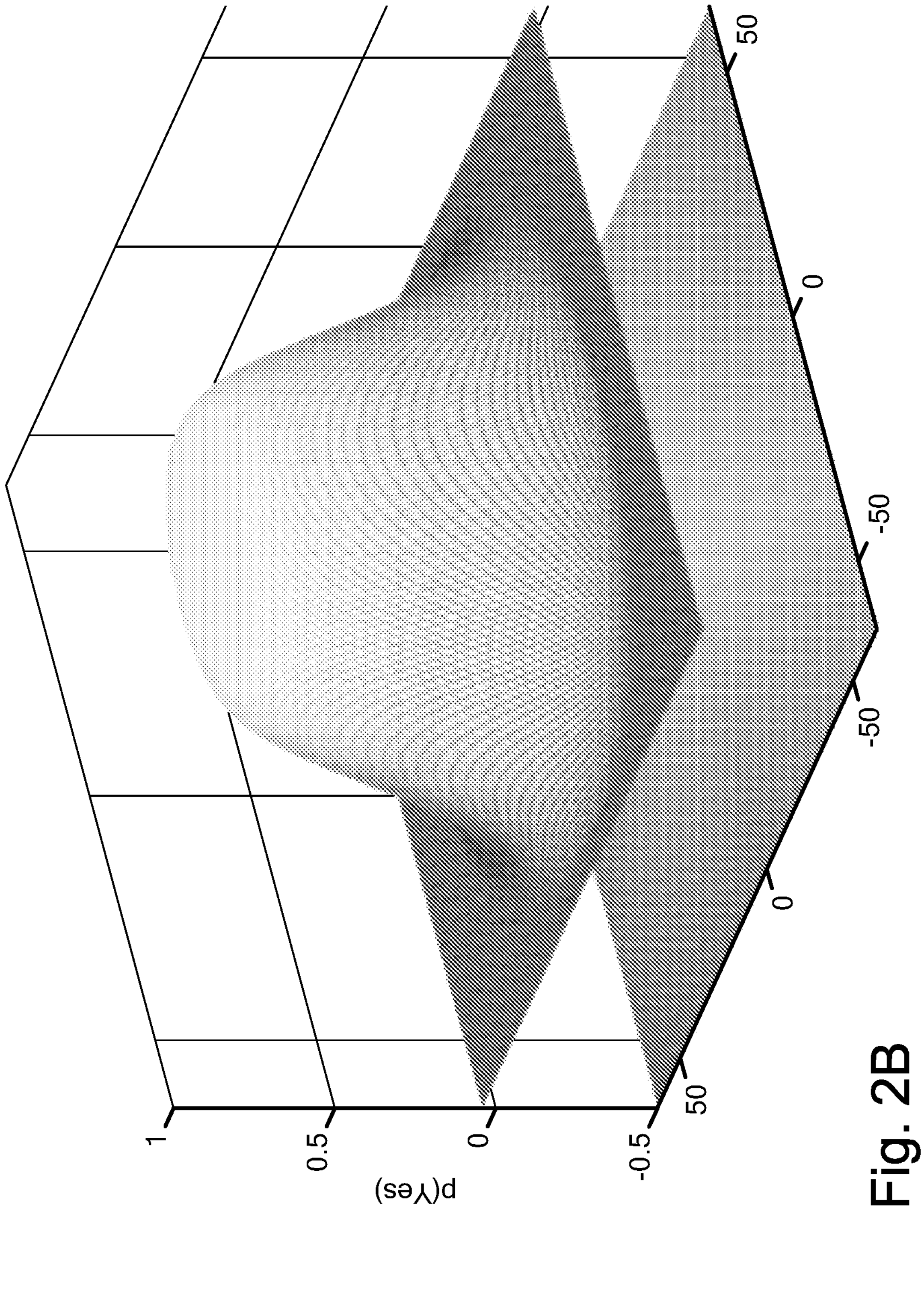
FIG. 2B shows a plot of the probability of reporting a stimulus as a function of hue saturation (color detection ellipse); stimulus color is shown on the lower plane.
Figure 2C:
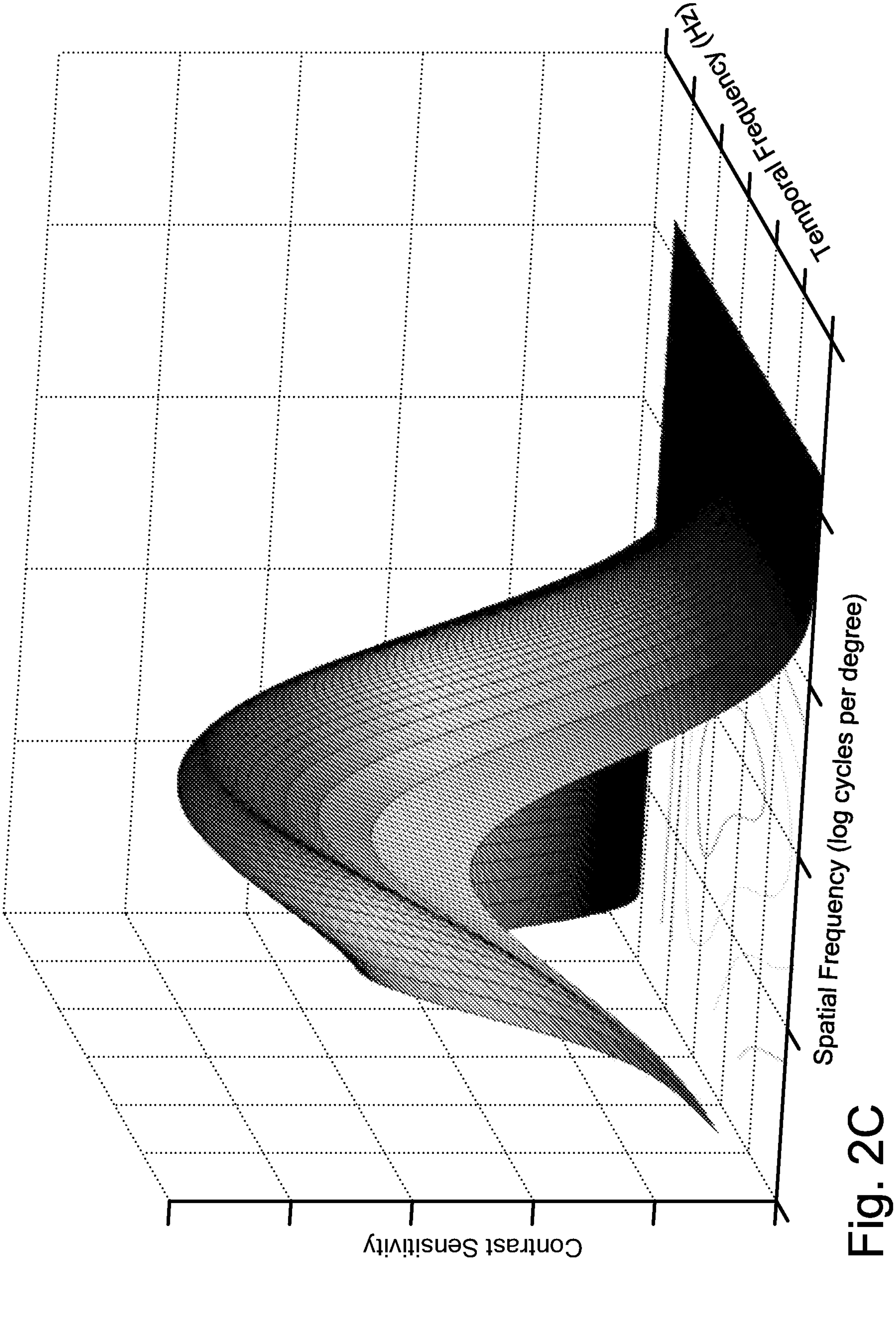
FIG. 2C shows a plot of a function depicting the probability of stimulus detection as a function of spatial frequency, temporal frequency, and contrast.

Psychometric formulas can be used to determine the threshold of stimulus characteristics, such as contrast or color, using a single stimulus dimension, such as spatial frequency for contrast, or hue for color. In many cases, functional forms for such thresholds are known. For example, a log parabola describes contrast sensitivity as a function of spatial frequency (FIG. 2A). An asymmetric ellipse describes color threshold as a function of hue (FIG. 2B) or the functional form of the temporal contrast sensitivity function. In these cases, the range of stimuli on each grid can be specified to cover the ongoing estimate of the potentially visible stimulus range (e.g., spatial frequency, hue, or temporal frequency) as well as the stimulus intensity (e.g., to span the ongoing estimate of d' from 0.1 to 4.5). FIG. 2 shows an example of the two-dimensional d' surface for the contrast sensitivity function and the color detection ellipse. This approach can be generalized to three dimensions (e.g., the spatio-temporal contrast sensitivity function, FIG. 2C) or even higher dimensional functions.

Summary data outputs from subject testing can include area under the log contrast sensitivity function, area under the threshold-versus contrast function, area under the chromatics sensitivity function, and volume under the spatio-temporal contrast sensitivity function when the functional form of the relationship between stimuli and sensitivity is known.

As an example, visual contrast sensitivity varies in two dimensions as a function of spatial frequency and contrast, according to the following relationship:

$$S_{LP}(f;f_0,b,a)=10^{-\left(\frac{\log_{10}(f/f_0)}{b}\right)^2}=1-a\ f<f_0\text{ and }s_{LP}<1-a.$$

(Watson & Ahumada, 2005, A Standard Model for Foveal Detection of Spatial Contrast, Journal of Vision, 5, 717-740).

As another example, visual contrast sensitivity varies in three dimensions as a function of spatial frequency, temporal frequency, and contrast, according to the following relationship:

$$CSF(\rho,v_R)=k\cdot c_0\cdot c_1\cdot c_2\cdot v_R\cdot(c_1 2\pi\rho)^2\exp\left(-\frac{c_1 4\pi\rho}{\rho_{max}}\right)$$

where $$k=s_1+s_2\cdot\left|\log\left(\frac{c_2 v_R}{3}\right)\right|^3$$

and, $$\rho_{max}=\frac{p_1}{(c_2 v_R+2)},$$

(D. Kelly, Motion and vision. II. Stabilized spatio-temporal threshold surface, *JOSA*, 69, pp. 1340-1349 (1979).

As yet another example, visual color sensitivity varies in two dimensions as a function of color saturation (k) and hue angle (h), according to an ellipse centered on the reference point (h,k):

$$\tau(s)=\frac{(x-h)^2}{a^2}+\frac{(y-k)^2}{b^2}$$

(W. R. J. Brown and D. L. MacAdam, "Visual Sensitivities to Combined Chromaticity and Luminance Differences*," J. Opt. Soc. Am. 39, 808-834 (1949)).

Figure 3:
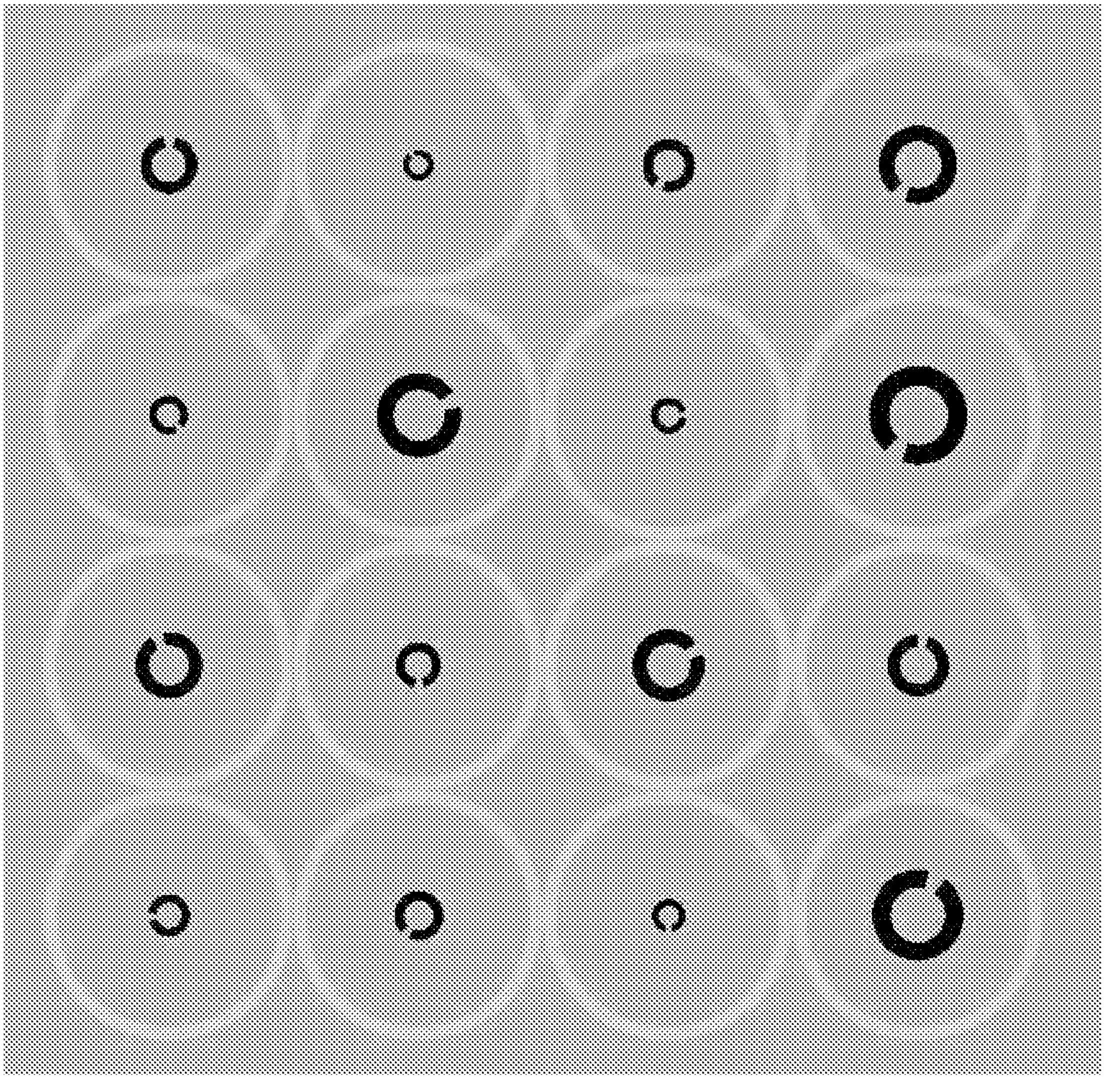
FIG. 3 shows a grid for assessing visual acuity. The subject indicates the orientation of the target arc (C-shaped structure) by clicking on the location on the cell wall (light gray circle) corresponding to the gap. For targets beyond the subject's resolution limit, the reported orientation is random (mean absolute error=90°). For targets above the resolution limit, orientation error may be elevated, but random (e.g., due to refractive error) or elevated and systematic (e.g., due to astigmatism). These errors provide additional information that is not provided by letter identification paradigms.

The above described methods can be used to assess visual acuity, which is typically measured with letter charts that are often pre-printed. The traditional method is slow, usually administered by a technician, requires the participant to know the Western alphabet (or to recognize child-friendly characters), and usually requires response scoring by a trained test administrator. The present technology can be used to measure visual acuity with the benefits of being rapid, intuitive, and administered in clinic or self-administrated at home. FIG. 3 illustrates an example grid for applying this method. As in standard visual acuity charts (e.g., logMAR and Snellen) the test begins with a series of stimuli that range from easy (20/200 equivalent) to difficult (20/10 equivalent) to span the range of visual acuity for the typically-sighted population. Stimuli outside this range can also be presented in the event that the subject accurately identifies all or none of the stimuli on the first chart. The algorithm can automatically increase the testing range in such cases. Each stimulus can be an oriented arc in which the line width is ⅕ of the stimulus diameter and the gap angle is equal to the line width, complaint with FDA acuity standards. Observers click on the ring to indicate the orientation of the arc. This is a continuous response, unlike a small number of choices of standard charts (10AFC for logMAR; 4AFC for HOTV, Landolt C or tumbling E). Moreover, the present test can be combined with other methods, such as band-pass filtering the stimuli to probe different regions of the spatial-processing visual pathway, or using colored stimuli. This allows an estimate of error, even for stimuli that are large enough to be identified, and can be diagnostic for conditions such as cataract and astigmatism and neuro-ophthalmic disorders such as age-related macular degeneration.

Figure 4A:
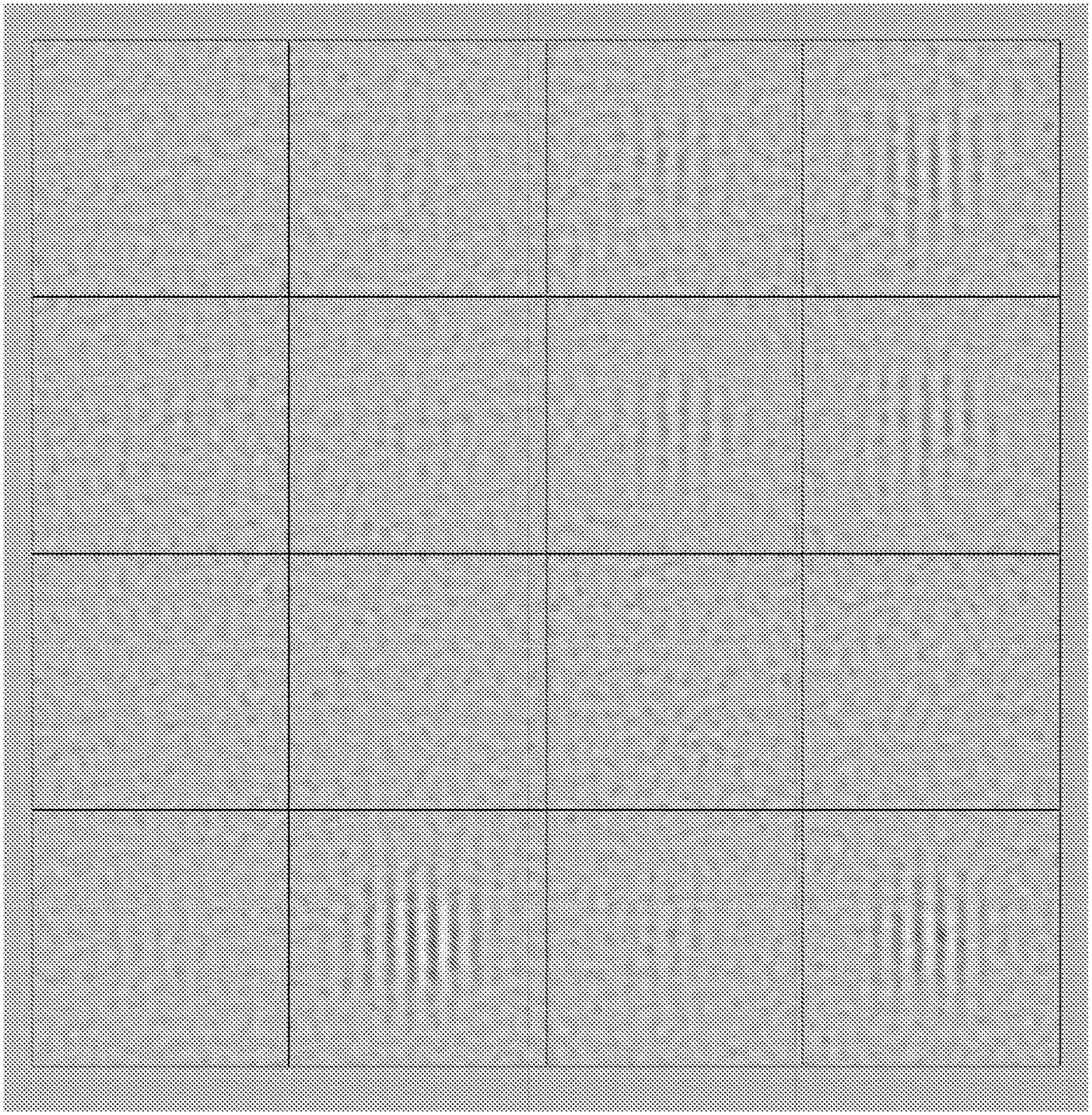
FIG. 4A shows a grid employing supra-threshold discrimination. This a variant of the grid shown in FIG. 1A. The subject is asked to click on each cell that contains a vertical grating. The grating as well as the background properties can be varied.
Figure 4B:
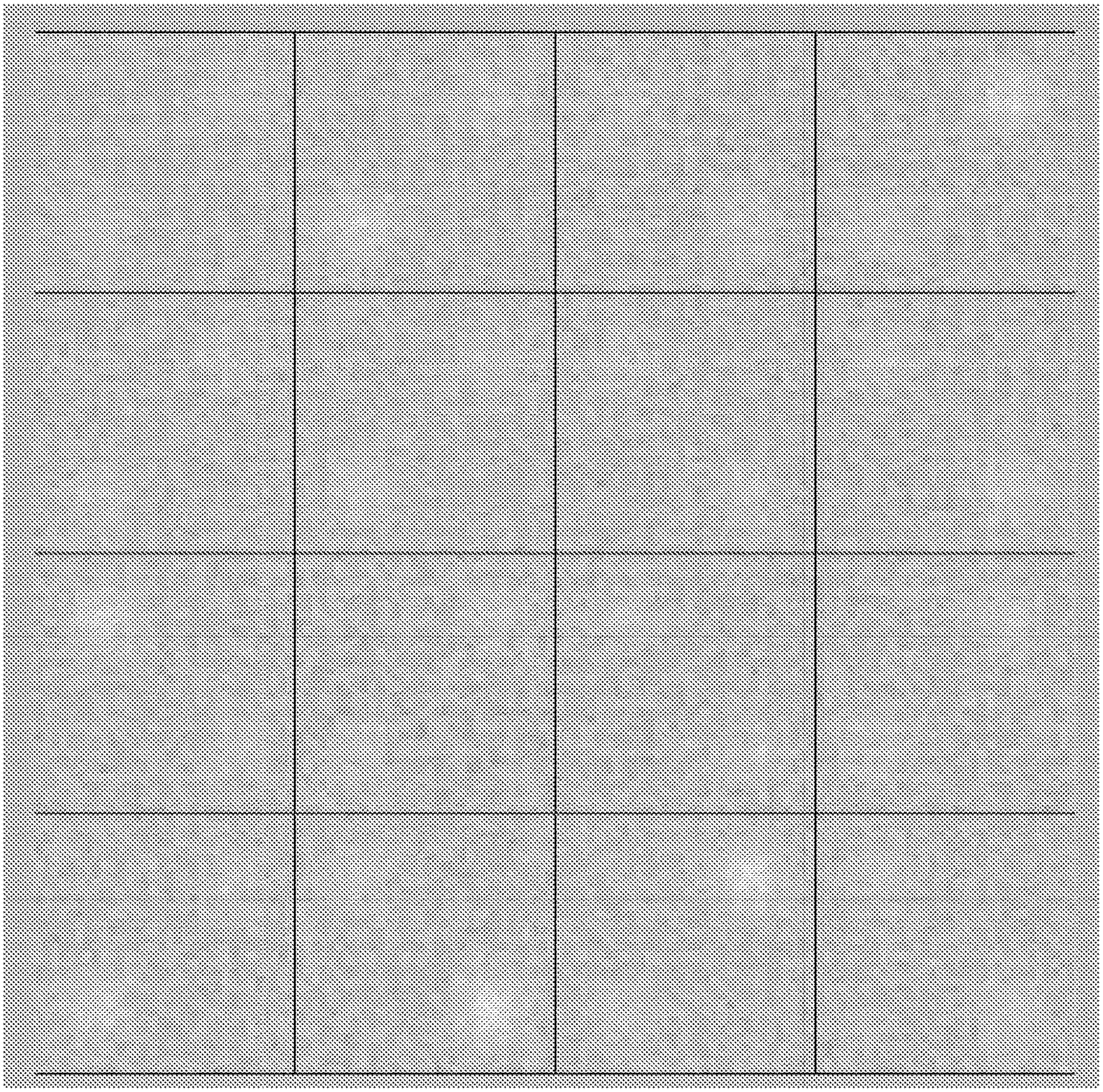
In FIG. 4B, the task is to click on each cell that contains two differently colored blobs. Again, the colors and background properties can be varied.

The present method can be extended to estimate supra-threshold discrimination performance, as well as threshold performance. FIG. 4A illustrates the measurement of a pedestal versus contrast stimulus, in which a target (here a Gabor patch) is presented on a background of varying contrast levels. Sensitivity to this stimulus is related to neuro-metric responses. FIG. 4B illustrates two examples, namely the measurement of contrast versus threshold (a) and color discrimination threshold (b) tasks. In this case, each cell contains more than one stimulus. In non-target cells the stimuli are the same hue, and in target cells the hue of the stimuli differs by a variable distance in color space. Observers select cells where the color of the elements differs, and the algorithm adaptively estimates threshold distances in color space. Whereas cone-contrast controlled color detection sensitivity (FIG. 1E) are diagnostic of retinal color deficits, suprathreshold color discrimination thresholds explore cortical chromatic processing.

Figure 5:
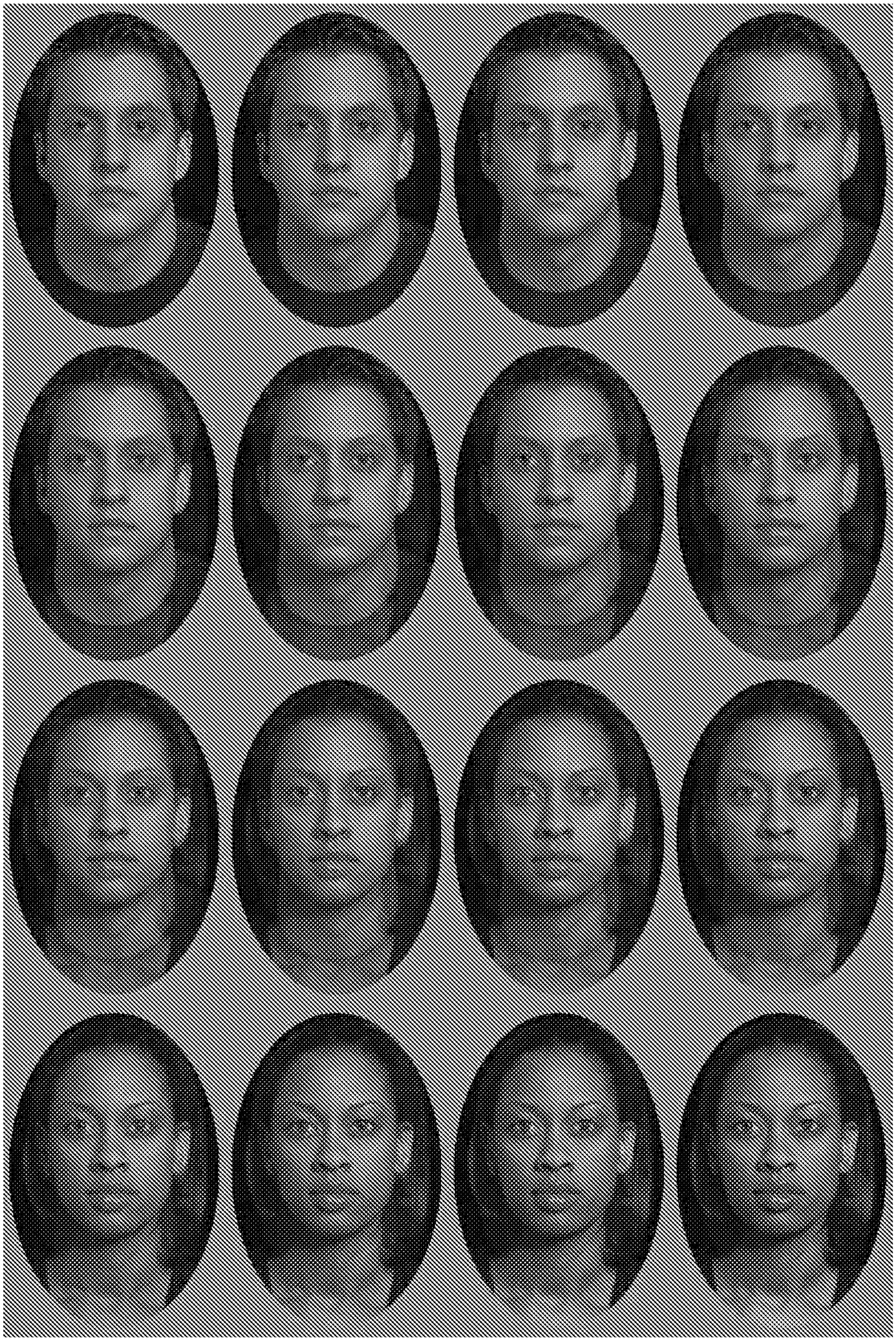
FIG. 5 shows a grid used for testing facial recognition using perceived gender as the variable. Each face is a blend of Individual A (top left) and Individual B (bottom right), with the contribution of B increasing down and to the right of the grid.

FIG. 5 illustrates an example of using facial recognition, perceived gender in this case, as a variable. Each face is a blend of Individual A (top left) and Individual B (bottom right), with the contribution of B increasing down and to the right of the figure.

Some neurological disorders selectively affect face processing. For example, the identification of individuals is impaired in prosopagnosia, and the recognition of emotional affect can be impaired in people with autism spectrum disorder. The technology can be extended to include target and non-target social cognition signals in order to detect the presence, progression, or remediation of social cognition impairment. FIG. 5 illustrates an example in which the identity of Individual A (top left) is progressively blended with Individual B (bottom right). The weights of the contribution of each individual, where the threshold (equally Individual A nor Individual B) and slope (rate at which the patient's decision changes) can be controlled by the algorithm adaptively between charts (grids). Variants of the paradigm can include emotional states such as anger, contempt, disgust, enjoyment, fear, sadness, or surprise, or their combinations that vary between cells. Age also can be used as a variable. Note that in order to eliminate luminance and chrominance cues to identity, the RGB histograms of the starting images can be adjusted and matched. Such methods can be used to quantify the accuracy and precision of social cue detection in neurotypical subjects and patients with neurological conditions. The approach also allows investigation of other areas of visual cognition, including object recognition or image complexity.

The present technology has the potential to address limitations of the prior art in the following ways. First, the test is very quick, so one or more tests can be administered conveniently in a single clinic visit or screening. Second, the same paradigm can employed using a plurality of different stimulus types, so that a comprehensive assessment of the function of different brain areas can be completed quickly and efficiently. Third, the same easy-to-understand protocol can be employed for all tests, so human subjects of all abilities can complete the test and do not need to learn a new protocol for different tests. Fourth, the test includes easy and difficult stimuli simultaneously, so subjects do not have to remember the test signal for the current task. Fifth, the test can be self-administered, so human subjects can complete tests at home, at work, when travelling, or on a sideline of a sporting event, without traveling to a clinic.

The present technology can be used to detect and/or monitor the progression of a range of ophthalmic diseases, including age-related macular degeneration, glaucoma, and amblyopia. Neurologic diseases or conditions, such as concussion, also can be diagnosed and/or monitored using the present technology. The technology can make a significant contribution to drug development for ophthalmic and neurologic diseases. The tests provided herein also can be used as an endpoint for optometric correction, such as correction involving contact lenses, spectacles, or intraocular lenses. The tests also can be used as an endpoint for treatment of neuro-ophthalmic disorders, including traumatic brain injury, head trauma, autism spectrum disorder, and attention deficit disorders. Table 1 summarizes how the technology can specifically diagnose a variety of visual and neurological conditions.

REFERENCES

1. Ravilla, D., & Holden, B. A. (2007). Uncorrected refractive error: The major and most easily avoidable cause of vision loss. Community Eye Health, 20(63), 3.
2. Davis, L. J., Schechtman, K. B., Wilson, B. S., Rosenstiel, C. E., Riley, C. H., Libassi, D. P., Gundel, R. E., Rosenberg, L., Gordon, M. O., & Zadnik, K. (2006). Longitudinal Changes in Visual Acuity in Keratoconus. 47(2), 12.
3. Levi, D. M. (2020). Rethinking amblyopia 2020. Vision Research, 176, 118-129.
4. Fleckenstein, M., Keenan, T. D. L., Guymer, R. H., Chakravarthy, U., Schmitz-Valckenberg, S., Klaver, C. C., Wong, W. T., & Chew, E. Y. (2021). Age-related macular degeneration. Nature Reviews Disease Primers, 7(1), 1-25.
5. Sample, P. A., Medeiros, F. A., Racette, L., Pascual, J. P., Boden, C., Zangwill, L. M., Bowd, C., & Weinreb, R. N. (2006). Identifying Glaucomatous Vision Loss with Visual-Function-Specific Perimetry in the Diagnostic Innovations in Glaucoma Study. Investigative Ophthalmology & Visual Science, 47(8), 3381-3389.
6. Willis, J. R., Doan, Q. V., Gleeson, M., Haskova, Z., Ramulu, P., Morse, L., & Cantrell, R. A. (2017). Vision-Related Functional Burden of Diabetic Retinopathy Across Severity Levels in the United States. JAMA Ophthalmology, 135(9), 926-932.

TABLE 1

Non-exhaustive list of targeted conditions with scientific references. Each test also quantifies typical or atypical development or age-related degeneration

| | | Test type | | | | | | | | | |
|---|---|---|---|---|---|---|---|---|---|---|---|
| | | Acuity | Spatial Contrast | Temporal Contrast | Color | Pattern | Motion | Depth | Dipper | Object | Faces |
| Condition Diagnosed | Refractive error [1] | x | x | ✓ | ✓ | ✓ | ✓ | ✓ | ✓ | ✓ | ✓ |
| | Keratoconus [2] | x | x | ✓ | ✓ | ✓ | ✓ | ✓ | ✓ | ✓ | ✓ |
| | Amblyopia [3] | x | x | ✓ | ✓ | x | x | x | ✓ | ✓ | ✓ |
| | Age-related Macular Degeneration [4] | x | x | ✓ | ✓ | x | ✓ | x | ✓ | ? | x |
| | Glaucoma [5] | ✓ | x | x | x | ✓ | x | ✓ | ✓ | ✓ | ✓ |
| | Diabetic Retinopathy [6] | x | x | ✓ | ✓ | ✓ | ✓ | ✓ | ✓ | ✓ | ✓ |
| | Color Vision Deficit[7] | ✓ | ✓ | ✓ | x | ✓ | ✓ | ✓ | ✓ | ✓ | ? |
| | Cataract [8] | ✓ | x | ✓ | x | ✓ | ✓ | ? | x | ✓ | ✓ |
| | Stroke* [9] | ✓ | x | x | x | x | x | x | x | x | x |
| | Traumatic Brain Injury* [10] | ✓ | x | x | x | x | x | x | x | x | x |
| | Brain lesion area V4 [11] | ✓ | ✓ | ✓ | x | x | ✓ | ✓ | ? | ✓ | ✓ |
| | Brain lesion area MT [12] | ✓ | ✓ | ✓ | ✓ | ✓ | x | ✓ | ? | ✓ | ✓ |
| | Brain lesion area FFA [13] | ✓ | ✓ | ✓ | ✓ | ✓ | ✓ | ✓ | ? | ✓ | x |
| | Alzheimer's Disease [14] | x | x | x | x | ✓ | x | ✓ | ? | ✓ | ✓ |
| | Parkinson's Disease [15] | x | x | x | x | ✓ | x | x | ? | x | x |
| | Prosopagnosia [16] | ✓ | ✓ | ✓ | ✓ | ✓ | ✓ | ✓ | ? | ✓ | x |
| | Object Agnosia [17] | ✓ | ✓ | ✓ | ✓ | ✓ | ✓ | ✓ | ? | x | ✓ |
| | Autism Spectrum Disorder [18] | ✓ | ✓ | ✓ | ✓ | x | x | ✓ | ? | ✓ | x |
| | Attention Deficit Disorder [19] | ✓ | x | ✓ | x | ? | ? | ? | ? | ? | ? |
| | Neurometric Response [20] | ✓ | x | ✓ | x | ? | ? | ? | ? | ? | ? |
| | Psychotic disorders[21] | ✓ | ✓ | ✓ | x | ? | x | ? | ? | ? | ? |
| | Post-traumatic stress disorder [22] | ✓ | x | ✓ | ✓ | ? | ✓ | x | ? | ? | x |
| | Obsessive compulsive disorder [23] | ? | ? | ? | ? | ? | x | ? | ? | ? | ? |
| | Big 5 Personality traits [24] | ✓ | ✓ | x | ✓ | ✓ | ✓ | ✓ | ✓ | ? | x |
| | Albinism [25] | x | x | x | x | ? | ? | ? | ? | ? | ? |
| | Prescription drug side-effects [26] | x | x | x | x | ? | ? | ? | ? | ? | ? |
| | Multiple Sclerosis[27] | x | x | x | x | ? | x | x | x | ? | ? |

*Pattern of deficits varies with locus of lesion

Key

✓ Within Normal Limits x Outside Normal Limits

? Not Currently Known

7. Hecht, S., & Shlaer, S. (1936). The Color Vision of Dichromats. The Journal of General Physiology, 20(1), 57-82.
8. Hurst, M. A., & Douthwaite, W. A. (1993). Assessing Vision Behind Cataract—A Review of Methods. Optometry and Vision Science, 70(11), 903-913.
9. Rowe, F. (2016). Visual effects and rehabilitation after stroke. Community Eye Health, 29(96), 75-76.
10. Armstrong, R. A. (2018). Visual problems associated with traumatic brain injury: Vision with traumatic brain injury. Clinical and Experimental Optometry, 101(6), 716-726.
11. Roe, A. W., Chelazzi, L., Connor, C. E., Conway, B. R., Fujita, I., Gallant, J. L., Lu, H., & Vanduffel, W. (2012). Toward a Unified Theory of Visual Area V4. Neuron, 74(1), 12-29.
12. Zeki, S. (1991). Cerebral akinetopsia (visual motion blindness). A review. Brain: A Journal of Neurology, 114 (Pt 2), 811-824.
13. Barton, J. J. S., Press, D. Z., Keenan, J. P., & O'Connor, M. (2002). Lesions of the fusiform face area impair perception of facial configuration in prosopagnosia. Neurology, 58(1), 71-78.
14. Salobrar-Garcia, E., Hoz, R. de, Ramirez, A. I., Lopez-Cuenca, I., Rojas, P., Vazirani, R., Amarante, C., Yubero, R., Gil, P., Pinazo-Duran, M. D., Salazar, J. J., & Ramirez, J. M. (2019). Changes in visual function and retinal structure in the progression of Alzheimer's disease. PLOS ONE, 14(8), e0220535.
15. Weil, R. S., Schrag, A. E., Warren, J. D., Crutch, S. J., Lees, A. J., & Morris, H. R. (2016). Visual dysfunction in Parkinson's disease. Brain, 139(11), 2827-2843.
16. Corrow, S. L., Dalrymple, K. A., & Barton, J. J. (2016). Prosopagnosia: Current perspectives. Eye and Brain, 8,165-175.
17. Greene, J. D. W. (2005). Apraxia, agnosias, and higher visual function abnormalities. Journal of Neurology, Neurosurgery & Psychiatry, 76(suppl 5), v25-v34.
18. Simmons, D. R., Robertson, A. E., McKay, L. S., Toal, E., McAleer, P., & Pollick, F. E. (2009). Vision in autism spectrum disorders. Vision Research, 49(22), 2705-2739.
19. Fuermaier, A. B. M., Hüpen, P., De Vries, S. M., Muller, M., Kok, F. M., Koerts, J., Heutink, J., Tucha, L., Gerlach, M., & Tucha, O. (2018). Perception in attention deficit hyperactivity disorder. ADHD Attention Deficit and Hyperactivity Disorders, 10(1), 21-47.
20. Boynton, G. M., Demb, J. B., Glover, G. H., & Heeger, D. J. (1999). Neuronal basis of contrast discrimination. Vision Research, 39(2), 257-269.
21. Kogata, T., & Iidaka, T. (2018). A review of impaired visual processing and the daily visual world in patients with schizophrenia. Nagoya Journal of Medical Science, 80(3), 317-328.
22. Trachtman, J. N. (2010). Post-traumatic stress disorder and vision. *Optometry-Journal of the American Optometric Association,* 81(5), 240-252.
23. Kim, J., Blake, R., Park, S., Shin, Y. W., Kang, D. H., & Kwon, J. S. (2008). Selective impairment in visual perception of biological motion in obsessive-compulsive disorder. *Depression and Anxiety,* 25(7), E15-E25.
24. Kachur, A., Osin, E., Davydov, D., Shutilov, K., & Novokshonov, A. (2020). Assessing the Big Five personality traits using real-life static facial images. *Scientific reports,* 10(1), 1-11.
25. Summers, C. G. (2009). Albinism: classification, clinical characteristics, and recent findings. *Optometry and vision Science,* 86(6), 659-662.
26. Li, J., Tripathi, R. C., & Tripathi, B. J. (2008). Drug-induced ocular disorders. Drug Safety: An International Journal of Medical Toxicology and Drug Experience, 31(2),127-141.
27. Balcer, L. J., Miller, D. H., Reingold, S. C., & Cohen, J. A. (2015). Vision and vision-related outcome measures in multiple sclerosis. Brain, 138(1), 11-27.

The present technology includes the following advantageous features:

i) Testing is extremely quick, and at least 10 times faster than comparable tests. A single comprehensive test can be performed in about 30 seconds, compared with 18 minutes with alternative methods.

ii) The testing method can be generalized to a broad range of tests for different visual pathways. Other tests require subjects to learn new stimuli and tasks for each test. Because the same method is employed in a broad range of tests, a more comprehensive assessment of the patient can be carried out.

iii) The test is intuitive and easy to administer. Other tests (e.g., letter acuity charts) require subjects to learn specific test items (e.g., the western alphabet), which complicates testing of either young, or non-western, or cognitively-impaired subjects.

iv) The test is adaptive. Each grid can be updated based on responses to successive stimuli, and each grid can contain both challenging and easy stimuli, which ensures the presence of exemplar stimuli and reduces memory demand for the task.

v) The test intentionally includes catch and null stimuli, which prevents cheating and eliminates the frustration of guessing that is encountered in other tests.

vi) The test can be self-administered and does not require a clinician or technician to proctor the test.

vii) The test can be administered away from a clinic, such as in the home, at a sports arena or battlefield, or for ecological momentary assessment. The ease and rapidity of administration can help identify impairment of visual pathway deficits earlier than alternative methods and can lead to earlier intervention and improved treatment outcomes.

The methods described herein can be implemented in any suitable computing system. The computing system can be implemented as or can include a computer device that includes a combination of hardware, software, and firmware that allows the computing device to run an applications layer or otherwise perform various processing tasks. Computing devices can include without limitation personal computers, work stations, servers, laptop computers, tablet computers, mobile devices, wireless devices, smartphones, wearable devices, embedded devices, microprocessor-based devices, microcontroller-based devices, programmable consumer electronics, mini-computers, main frame computers, and the like and combinations thereof.

Processing tasks can be carried out by one or more processors. Various types of processing technology can be used including a single processor or multiple processors, a central processing unit (CPU), multicore processors, parallel processors, or distributed processors. Additional specialized processing resources such as graphics (e.g., a graphics processing unit or GPU), video, multimedia, or mathematical processing capabilities can be provided to perform certain processing tasks. Processing tasks can be implemented with computer-executable instructions, such as application programs or other program modules, executed by the computing device. Application programs and program modules can include routines, subroutines, programs, scripts, drivers, objects, components, data structures, and the like that perform particular tasks or operate on data.

Processors can include one or more logic devices, such as small-scale integrated circuits, programmable logic arrays, programmable logic devices, masked-programmed gate arrays, field programmable gate arrays (FPGAs), application specific integrated circuits (ASICs), and complex programmable logic devices (CPLDs). Logic devices can include, without limitation, arithmetic logic blocks and operators, registers, finite state machines, multiplexers, accumulators, comparators, counters, look-up tables, gates, latches, flip-flops, input and output ports, carry in and carry out ports, and parity generators, and interconnection resources for logic blocks, logic units and logic cells.

The computing device includes memory or storage, which can be accessed by a system bus or in any other manner. Memory can store control logic, instructions, and/or data. Memory can include transitory memory, such as cache memory, random access memory (RAM), static random access memory (SRAM), main memory, dynamic random access memory (DRAM), block random access memory (BRAM), and memristor memory cells. Memory can include storage for firmware or microcode, such as programmable read only memory (PROM) and erasable programmable read only memory (EPROM). Memory can include non-transitory or nonvolatile or persistent memory such as read only memory (ROM), one time programmable non-volatile memory (OTPNVM), hard disk drives, optical storage devices, compact disc drives, flash drives, floppy disk drives, magnetic tape drives, memory chips, and memristor memory cells. Non-transitory memory can be provided on a removable storage device. A computer-readable medium can include any physical medium that is capable of encoding instructions and/or storing data that can be subsequently used by a processor to implement embodiments of the systems and methods described herein. Physical media can include floppy discs, optical discs, CDs, mini-CDs, DVDs, HD-DVDs, Blu-ray discs, hard drives, tape drives, flash memory, or memory chips. Any other type of tangible, non-transitory storage that can provide instructions and/or data to a processor can be used in the systems and methods described herein.

The computing device can include one or more input/output interfaces for connecting input and output devices to various other components of the computing device. Input and output devices can include, without limitation, keyboards, mice, joysticks, microphones, cameras, webcams, displays, touchscreens, monitors, scanners, speakers, and printers. Interfaces can include universal serial bus (USB) ports, serial ports, parallel ports, game ports, and the like.

The computing device can access a network over a network connection that provides the computing device with telecommunications capabilities Network connection enables the computing device to communicate and interact with any combination of remote devices, remote networks, and remote entities via a communications link. The communications link can be any type of communication link including without limitation a wired or wireless link. For example, the network connection can allow the computing device to communicate with remote devices over a network which can be a wired and/or a wireless network, and which can include any combination of intranet, local area networks (LANs), enterprise-wide networks, medium area networks, wide area networks (WANS), virtual private networks (VPNs), the Internet, cellular networks, and the like. Control logic and/or data can be transmitted to and from the computing device via the network connection. The network connection can include a modem, a network interface (such as an Ethernet card), a communication port, a PCMCIA slot and card, or the like to enable transmission to and receipt of data via the communications link. A transceiver can include one or more devices that both transmit and receive signals, whether sharing common circuitry, housing, or a circuit boards, or whether distributed over separated circuitry, housings, or circuit boards, and can include a transmitter-receiver.

The computing device can include a browser and a display that allow a user to browse and view pages or other content served by a web server over the communications link. A web server, sever, and database can be located at the same or at different locations and can be part of the same computing device, different computing devices, or distributed across a network. A data center can be located at a remote location and accessed by the computing device over a network. The computer system can include architecture distributed over one or more networks, such as, for example, a cloud computing architecture. Cloud computing includes without limitation distributed network architectures for providing, for example, software as a service (SaaS).

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with the alternative expressions "consisting essentially of" or "consisting of".

The invention claimed is:

1. A method for characterizing responsiveness to a visual stimulus by a human subject, the method comprising:

(a) providing a device having a graphical display and a user input;

(b) displaying sequentially a plurality of grids on the display, each grid comprising a plurality of cells arranged in two dimensions on the graphical display;
 wherein each grid comprises a visual stimulus displayed in two or more of the cells of the grid;
 wherein the visual stimulus displayed within a grid varies in intensity from cell to cell; and
 wherein the stimulus displayed for each grid differs from the stimulus displayed by at least one other grid of the plurality of grids;

(c) receiving subject responses through the user input, the responses indicating a perceived characteristic of the stimulus for each cell of each displayed grid; and (d) analyzing the subject responses from each grid using a sensitivity function to obtain the subject's responsiveness to each of the stimuli in the plurality of grids, said responsiveness characterized as a probability of reporting the stimulus as a function of stimulus intensity;

wherein the sensitivity function is a d-prime function, defined as:

$$d'(s) = \frac{\beta(s/\tau)^{\gamma}}{\sqrt{(\beta^2 - 1) + (s/\tau)^{2\gamma}}}$$

where $\tau$ is the sensitivity threshold (stimulus intensity where d'=1), $\beta$ is an upper asymptote of the saturating function (stimulus intensity where d'=5), s is signal intensity, and $\gamma$ is slope of the function; and wherein d'(s) is related to the probability of the subject reporting the presence of the stimulus as a function of stimulus intensity by the following psychometric function:

$$\Psi_{yes}(s) = 1 - G(z(1 - \Psi_{yes}(0) - d'(s))$$

where G(s) is a cumulative Gaussian function, z is a z-score, and $\Psi_{yes}(0)$ is false alarm rate.

2. The method of claim 1, further comprising:

(e) analyzing the subject's responsiveness to two or more different stimuli of the plurality of grids to obtain a pattern of responsiveness of the subject.

3. The method of claim 2, further comprising:

(f) comparing the subject's pattern of responsiveness to one or more known patterns of responsiveness; and (g) identifying a presence or absence in the subject, or a likelihood thereof, of one or more visual or neurological conditions.

4. The method of claim 1, wherein the perceived characteristic of the stimulus comprises one or more stimulus characteristics selected from the group consisting of absence, presence, luminance, contrast, color, depth, motion, flicker, spatial form, object recognition, object shape, object form, object size, facial recognition, facial feature recognition, feature position, feature angle, spatial resolution, noise-defined depth, and sparse-pattern depth.

5. The method of claim 1, wherein the stimulus intensity within a grid spans a range from difficult to detect to easy to detect for the subject.

6. The method of claim 1, wherein the position of stimulus-containing cells within the grid is random or non-random.

7. The method of claim 1, wherein the stimuli in the cells of each grid are displayed only one at a time, with all other cells of the grid remaining blank until the subject's response is obtained for the displayed cell.

8. The method of claim 1, wherein the cells of one or more grids are arranged in rows and columns.

9. The method of claim 1, wherein one or more grids are displayed for each stimulus.

10. The method of claim 1, wherein stimulus type or stimulus intensity within a grid is varied from an earlier presented grid based upon subject responses.

11. The method of claim 1, wherein the subject responds for each cell of a grid whether the stimulus is present or not present in the cell, and wherein the subject's sensitivity to the stimulus is calculated.

12. The method of claim 1, wherein the subject indicates a degree of confidence in their response for each cell based on a position of their response or a secondary response.

13. The method of claim 1, wherein the psychometric function is computed on-the-fly for each grid and is used to estimate a stimulus for which d'=0.1, which is very difficult for the subject to detect, and a stimulus intensity for which d'=4.5, which is very easy for the subject to detect.

14. The method of claim 1, wherein the test is optimized for the subject by performing two or more trials of the plurality of grids, wherein the stimulus intensities on a first trial are based on data from previous observers or on physical stimulus limits of the display, and wherein the stimulus intensities on subsequent trials are based on the estimate of sensitivity computed for all previous grids for the current observer.

15. The method of claim 1, wherein both threshold stimulus intensity and suprathreshold performance of the subject are determined.

16. The method of claim 1, wherein individual cells comprise two or more stimuli, and the subject's response comprises discrimination between the two or more stimuli.

17. The method of claim 1, wherein sensitivity to one or more of the stimuli can vary in two or more dimensions, and wherein a known relationship exists between said one or more stimuli and two or more types of subject sensitivity thereto.

18. The method of claim 17, wherein the two or more types of subject sensitivity comprise spatial frequency and contrast, and wherein the known relationship is defined by:

$$S_{LP}(f : f_0 \cdot b \cdot a) = 10^{\left(\frac{log_{10}(f/f_0)}{b}\right)^2} = 1 - a \;\; f < f_0 \text{ and } s_{LP} < 1 - a.$$

19. The method of claim 17, wherein the two or more types of subject sensitivity comprise spatial frequency, temporal frequency, and contrast, and wherein the known relationship is defined by:

$$CSF(\rho, v_R) = k \cdot c_0 \cdot c_1 \cdot c_2 \cdot v_R \cdot (c_1 2\pi\rho)^2 \exp\left(-\frac{c_1 4\pi\rho}{\rho_{max}}\right)$$

where $$k = s_1 + s_2 \cdot \left|\log\left(\frac{c_2 v_R}{3}\right)\right|^3$$

and, $$\rho_{max} = \frac{p_1}{(c_2 v_R + 2)},$$

20. The method of claim 17, wherein the two or more types of subject sensitivity comprise color saturation and hue angle, and wherein the known relationship is defined by:

$$\tau(s) = \frac{(x-h)^2}{a^2} + \frac{(y-k)^2}{b^2}$$

wherein $\tau$ is visual color sensitivity for stimulus sensitivity s, h is hue angle, and k is color saturation.

21. The method of claim 17, wherein the two or more types of subject sensitivity comprise stimulus variance and response variance, and wherein the known relationship is defined by an equivalent noise function defined as:

$$\tau(s) = \sqrt{\frac{\sigma_{int}^2 + \sigma_{ext}^2}{N_{samp}}}$$

wherein $\tau$ is visual detection threshold for stimulus intensity s, $\sigma_{int}$ is intrinsic noise in the observer's visual system, $\sigma_{iex}$ is external noise in the stimulus, and $N_{samp}$ is sampling efficiency, corresponding to the number of stimulus samples employed by the observer.

22. The method of claim 17, wherein the two or more types of subject sensitivity comprise stimulus pedestal intensity and sensitivity, and wherein the known relationship is defined by a dipper or threshold versus intensity function defined as:

$$\tau(s) = \sqrt{\left(1 + \frac{1}{S}\right)\left(\sigma_{int}^2 + \sigma_{ext}^2\right)} - \sigma_{ext}$$

wherein $\tau$ is visual detection threshold for stimulus intensity s, $\sigma_{int}$ is intrinsic noise in the observer's visual system, $\sigma_{iex}$ is the intensity of the stimulus pedestal, and S is the discrimination criterion employed by the observer.

23. The method of claim 1, wherein the subject provides responses using a touch-sensitive display screen, computer pointing device, or speech recognition software.

24. The method of claim 1, wherein the method is supervised or self-administered by the subject outside of a medical facility, vision testing facility, or doctor's office.

25. The method of claim 1, wherein the method is repeated after one or more time intervals.

26. The method of claim 1, wherein the method is used to detect and/or monitor the progression of an ophthalmic condition, an optometric condition, or a neurologic disease or condition.

27. The method of claim 26, wherein the ophthalmic disease or condition is selected from the group consisting of age-related macular degeneration and other disorders of early visual neural pathways; diabetic retinopathy; color vision deficit; glaucoma; and amblyopia.

28. The method of claim 26, wherein the optometric condition is selected from the group consisting of myopia, hyperopia, astigmatism and other optical aberrations of lower and higher order; presbyopia; and cataract, corneal edema, and other changes in optical opacity.

29. The method of claim 26, wherein the neurologic disease or condition is selected from the group consisting of concussion, traumatic brain injury, traumatic eye injury, and other types of neurological trauma; cognitive impairment, Autism Spectrum Condition (ASC), Attention Deficit Disorder (ADD), and other high level neurological disorders; and schizophrenia, depression, bipolar disorder, and other psychotic disorders.

30. The method of claim 26, wherein said detection and/or monitoring of the progression of an ophthalmic condition, an optometric condition, or a neurologic disease or condition comprises analysis of a pattern of sensitivities.

31. A method for characterizing responsiveness to a visual stimulus by a human subject, the method comprising:

(a) providing a device having a graphical display and a user input;

(b) displaying sequentially a plurality of grids on the display, each grid comprising a plurality of cells arranged in two dimensions on the graphical display;

wherein each grid comprises a visual stimulus displayed in two or more of the cells of the grid;

wherein the visual stimulus displayed within a grid varies in intensity from cell to cell; and wherein the stimulus displayed for each grid differs from the stimulus displayed by at least one other grid of the plurality of grids;

(c) receiving subject responses through the user input, the responses indicating a perceived characteristic of the stimulus for each cell of each displayed grid; and (d) analyzing the subject responses from each grid using a sensitivity function to obtain the subject's responsiveness to each of the stimuli in the plurality of grids, said responsiveness characterized as a probability of reporting the stimulus as a function of stimulus intensity, wherein the sensitivity function is an orientation error function, defined as:

$$\tau_\theta(s) = \left(\theta_i + \left(\frac{\pi}{2} - \theta_i\right)\right)\left(0.5 + 0.5 * \operatorname{erf}\left(\frac{s - \tau}{\sqrt{2}\gamma}\right)\right)$$

where $\tau$ is a sensitivity threshold, $\theta_i$ is intrinsic orientation uncertainty within the subject's visual system, s is signal intensity and $\gamma$ is the slope of the function.

32. A method for characterizing responsiveness to a visual stimulus by a human subject, the method comprising:

(a) providing a device having a graphical display and a user input;

(b) displaying sequentially a plurality of grids on the display, each grid comprising a plurality of cells arranged in two dimensions on the graphical display;

wherein each grid comprises a visual stimulus displayed in two or more of the cells of the grid;

wherein the visual stimulus displayed within a grid varies in intensity from cell to cell; and wherein the stimulus displayed for each grid differs from the stimulus displayed by at least one other grid of the plurality of grids;

(c) receiving subject responses through the user input, the responses indicating a perceived characteristic of the stimulus for each cell of each displayed grid; and (d) analyzing the subject responses from each grid using a sensitivity function to obtain the subject's responsiveness to each of the stimuli in the plurality of grids, said responsiveness characterized as a probability of reporting the stimulus as a function of stimulus intensity, wherein the sensitivity function is a cumulative Gaussian function, defined as:

$$\tau(s) = (p_{guess} + (1 - p_{guess}))\left(0.5 + 0.5 * \operatorname{erf}\left(\frac{s - \tau}{\sqrt{2}\gamma}\right)\right)$$

where $\tau$ is a sensitivity threshold, $P_{guess}$ is the probability of a correct response for a guess (equal to the reciprocal of the number of alternative response choices), s is signal intensity and $\gamma$ is the slope of the sensitivity function.

* * * * *